(12) United States Patent
Karli et al.

(10) Patent No.: US 9,840,690 B2
(45) Date of Patent: *Dec. 12, 2017

(54) SYSTEMS AND METHODS FOR AUTOLOGOUS BIOLOGICAL THERAPEUTICS

(71) Applicant: Greyledge Technologies LLC, Vail, CO (US)

(72) Inventors: David Karli, Edwards, CO (US); David L. Bombard, Edwards, CO (US)

(73) Assignee: Greyledge Technologies, LLC, Vail, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,073

(22) Filed: Sep. 8, 2015

(65) Prior Publication Data

US 2015/0376564 A1 Dec. 31, 2015

Related U.S. Application Data

(63) Continuation of application No. 13/421,728, filed on Mar. 15, 2012, now Pat. No. 9,164,079.

(Continued)

(51) Int. Cl.
*C12M 1/26* (2006.01)
*C12M 1/34* (2006.01)
(Continued)

(52) U.S. Cl.
CPC .............. *C12M 33/10* (2013.01); *A61K 35/16* (2013.01); *A61K 35/19* (2013.01); *A61K 35/28* (2013.01);
(Continued)

(58) Field of Classification Search
CPC .................................................. G01N 33/491
See application file for complete search history.

(56) References Cited

U.S. PATENT DOCUMENTS 4,851,126 A  7/1989 Schoendorfer
4,944,883 A  7/1990 Schoendorfer et al.
(Continued)

FOREIGN PATENT DOCUMENTS

CA  2124812 C  4/1994
CN  1300233 A  6/2001
(Continued)

OTHER PUBLICATIONS

YouTube video of Angel PRP whole blood separation device published online Oct. 12, 2010. Retreived at https://www.youtube.com/watch?v=b0f2NnVIQag . Includes screenshots.*

(Continued)

*Primary Examiner* — Jill Warden
*Assistant Examiner* — Benjamin R Whatley
(74) *Attorney, Agent, or Firm* — Winstead PC

(57) ABSTRACT

An autologous cell concentrating system and method are disclosed. The system has a blood separation component, a first vessel, a second vessel, a first valve, a second valve, and a concentration and flow logic and control component. The concentration and flow logic and control component is configured to: determine a first volume of a target cell-poor fraction in the first vessel to mix with a target cell-rich fraction in the second vessel in order to form a target cell-rich concentrate having a concentration of target cells that is within a target concentration range; and control the second valve to transfer the first volume of the target cell-rich fraction from the first vessel to the second vessel to form the target cell-rich concentrate. The target concentration range is between 1.0 and $1.5 \times 10^6$ target cells/µL.

6 Claims, 14 Drawing Sheets

Related U.S. Application Data

(60) Provisional application No. 61/453,658, filed on Mar. 17, 2011.

(51) Int. Cl.
    *A61M 1/38*     (2006.01)
    *G01N 33/49*     (2006.01)
    *A61K 35/16*     (2015.01)
    *A61K 35/28*     (2015.01)
    *A61K 35/19*     (2015.01)

(52) U.S. Cl.
    CPC .............. *A61M 1/382* (2013.01); *C12M 41/36* (2013.01); *G01N 33/491* (2013.01)

(56) References Cited

U.S. PATENT DOCUMENTS

| | | | |
|---|---|---|---|
| 5,135,667 | A | 8/1992 | Schoendorfer |
| 5,817,519 | A | 10/1998 | Zelmanovic et al. |
| 5,958,250 | A | 9/1999 | Brown et al. |
| 6,025,201 | A | 2/2000 | Zelmanovic et al. |
| 6,261,549 | B1 | 7/2001 | Fernandez et al. |
| 6,312,607 | B1 | 11/2001 | Brown et al. |
| 6,790,371 | B2 | 9/2004 | Dolecek |
| 6,855,119 | B2 | 2/2005 | Rivera et al. |
| 6,887,371 | B2 | 5/2005 | Dolecek |
| 7,252,758 | B2 | 8/2007 | Dolecek et al. |
| 7,262,059 | B2 | 8/2007 | Zheng et al. |
| 7,393,690 | B2 | 7/2008 | Sukavaneshvar et al. |
| 7,824,559 | B2 | 11/2010 | Dorian et al. |
| 7,832,566 | B2 | 11/2010 | Leach et al. |
| 7,837,884 | B2 | 11/2010 | Dorian et al. |
| 7,867,159 | B2 | 1/2011 | Dolecek et al. |
| 7,906,338 | B2 | 3/2011 | Sukavaneshvar et al. |
| 9,164,079 | B2 * | 10/2015 | Karli ................... G01N 33/491 |
| 2003/0066807 | A1 | 4/2003 | Suzuki |
| 2005/0269251 | A1* | 12/2005 | Cork ................... A61B 5/14546 210/85 |
| 2009/0215602 | A1 | 8/2009 | Min et al. |
| 2010/0112081 | A1 | 5/2010 | Mishra et al. |
| 2010/0137161 | A1 | 6/2010 | Peace et al. |
| 2010/0221230 | A1 | 9/2010 | Hirose et al. |

FOREIGN PATENT DOCUMENTS

| | | |
|---|---|---|
| CN | 102262090 A | 11/2011 |
| WO | 0061256 A1 | 10/2000 |

OTHER PUBLICATIONS

Cytomedix Regenerative Biotherapies, "Angel Whole Blood Separation", "Product Guide", 2010, p. 4, Publisher: Cytomedix, Inc., Published in: US.

Boteler, D., et al., "Lab-on-a-Chip White Blood Cell Counter", "MicroNanoBio Final Paper", Apr. 29, 2005, p. 11, Publisher: U. of Colo., Published in: US.

Browne, A.W., et al., "A lab-on-a-chip for rapid blood separation and quantification of hematocrit and serum analytes", "Lab on a Chip article downloaded Sep. 14, 2011 from http://pubs.rsc.org/loc", Jun. 8, 2011, pp. 2440-2446, vol. 2011, No. 11, Publisher: The Royal Soc'y of Chem., Published in: US.

Cho, et al., "Effect of platelet-rich plasma on ultraviolet b-induced skin wrinkles in nude mice", Aug. 12, 2010, p. 9, Publisher: Dept. of plastic and Reconstructive Surgery, Seoul National University College of Medicine, Published in: KR.

Choi, S., et al., "Continuous blood cell separation by hydrophoretic filtration", "Lab on a Chip article downloaded Sep. 8, 2011 from http://pubs.rcs.org", Aug. 10, 2007, pp. 1532-1538, vol. 2007, No. 7, Publisher: The Royal Soc'y of Chem., Published in: US.

Xiaodong, Liu, "Chinese Office Action re Application No. 201280018114.8", Mar. 20, 2015, p. 12, Published in: CN.

Xiaodong, Liu, "Chinese Office Action re Application No. 201280018114.8", Jun. 27, 2014, p. 21, Published in: CN.

Xiaodong, Liu, "CN Response to Office Action re Application No. 201280018114.8", Jan. 12, 2015, p. 14, Published in: CN.

Xiaodong, Liu, "CN Response to Office Action re Application No. 201280018114.8", Jun. 4, 2015, p. 12, Published in: CN.

Dimov, I.K., et al., "Stand-alone self-powered integrated microfluidic blood analysis system (SIMBAS)", "Lab on a Chip article downloaded Sep. 9, 2011 from http:pubs.rsc.org", Mar. 7, 2011, pp. 845-850, vol. 11, No. 5, Publisher: The Royal Soc'y of Chem. Publishing, Published in: US.

Piling, Stephen, "Extended European Search Report re Application No. 12757514.0", Sep. 1, 2014, p. 9, Published in: EP.

Everts, et al., "Platelet-Rish Plasma and Platelet Gel: A Review", 2006, p. 14, Publisher: The Journal of The American Society of Extra-Corporeal Technology.

Everts, "Autologous Platelet-Leukocyte Enriched Gel—Basics and Efficacy", 2007, p. 6.

Exactech Biologics, "Accelerate Concentrating System—Preparation Technique", "Product Guide", 2010, p. 3, Publisher: Exactech, Inc., Published in: US.

Foster, et al., "Platelet-Rich Plasma", 2009, p. 14, Publisher: The American Journal of Sports Medicine, Published in: US.

Inglis, D.W., et al., "Microfluidic device for label-free measurement of platelet activation", "Lab on a Chip", 2008, p. 9, Publisher: The Royal Soc'y of Chem., Published in: US.

Kersaudy-Kerhoas, M., et al., "Hydrodynamic blood plasma separation in microfluidic channels", "Micofluid Nanofluid—Research Paper", May 8, 2009, pp. 105-114, vol. 2010, No. 8, Publisher: Springer-Verlag.

Kevy, et al., "Platelet-Rish Plasma", "Inventor aware of prior art on or before May 19, 2015", , p. 20, Published in: US.

Lopez-Vidriero, et al., "The Use of Platelet-Rish Plasma in Arthroscopy and Sports Medicine: Optimizing the Healing Environment", Feb. 2010, p. 10, Publisher: Arthroscopy: The Journal of Arthroscopic and Related Surgery.

Marx, "Platelet-Rish Plasma: Evidence to Support Its Use", 2004, Publisher: American Association of Oral and Maxillofacial Surgeons, Published in: US.

Mastrangelo, et al., "Reduce Platelet Concentration Does Not Harm PRP Effectiveness for ACL Repair in a Porcine in Vivo Model", Jan. 6, 2011, p. 6, Published in: US.

Mazzucco, et al., "The Use of Autologous Platelet Gel to Treat Difficult-to-Heal Wounds: A Pilot Study", Jul. 2004, p. 8, Publisher: Transfusion, Published in: US.

Milano, et al, "The Effect of Platelet Rich Plasma Combined with Microfractures on the Treatment of Chonral Defects: An Experimental Study in a Sheep Model", Mar. 31, 2010, Publisher: Osteoarthritis Research Society International, Published in: US.

Young, Lee W., "International Search Report and Written Opinion re Application No. PCT/US2012/029379", dated Jun. 19, 2012, p. 9, Published in: PCT.

Becamel, Philippe, "International Preliminary Report on Patentability re Application No. PCT/US2012/029379", dated Sep. 26, 2013, p. 7, Published in: CH.

Pinkowski, R., "Difference between impedance and optical platelet count methods in patients with microcytosis of red blood cells", "Laboratory Hematology", Jun. 22, 1999, pp. 22-27, vol. 1999, No. 5, Publisher: Carden Jennings Publishing Co., Ltd.

Pommer, M.S., et al., "Dielectrophoretic separation of platelets from diluted whole blood in microfluidic channels", "Electrophoresis—Microfluidics and Miniaturization", Oct. 1, 2007, pp. 1213-1218, vol. 2008, No. 29, Publisher: Wiley-VCH Verlag GmbH & Co. KGaA, Weinheim, Published in: DE.

"Platelet-Rich Plasma (PRP)/Platelet Gel Device Summary", "Webpage found at http://www.perfusion.com/perfusion/prpdevicesummary.asp downloaded on", Feb. 18, 2011, p. 3, Publisher: Perfusion, Published in: US.

Bombard, David, "Review of PRP Options: Industry Automated Devices", "Power Point Presentation", 2011, p. 19, Published in: US.

(56) References Cited

OTHER PUBLICATIONS

Global Data, "Platelet Rich Plasma: A Market Snapshot", "Market Analysis Alert", May 2010, p. 8, Publisher: GlobalData, Published in: US.

Sanchez, et al., "Comparison of Surgically Repaired Achilles Tnedon Tears Using Platelet-Rich Fibrin Matrices", Nov. 12, 2006, Publisher: American Journal of Sports Medicine, Published in: US.

Schafer, D., et al., "Microfluidic cell counter with embedded optical fibers fabricated by femtosecond laser ablation and anodic bonding", "Optics Express", Apr. 13, 2009, pp. 6068-6073, vol. 17, No. 8, Publisher: Optical Soc'y of Am., Published in: US.

Sumida, E., et al., "Platelet Separation From Whole Blood in an Aqueous Two-Phase System With Water-Soluble Polymers", "J. Pharmacol. Sci.", , pp. 91-97, vol. 2006, No. 101, Publisher: The Japanese Pharmacological Soc'y.

Weibrich, et al., "Effect of Platelet Concentration in Platelet-rish plasma on peri-implant bone regeneration", Dec. 4, 2003, p. 7, Publisher: Elsevier, Published in: US.

Woodell-May, et al., "Producing Accurate Platelet Counts for Platelet Rish Plasma: Validation of a Hematology Analyzer and Preparation Techniques for Counting", Jan. 24, 2005, p. 9, Publisher: Journal of Craniofacial Surgery, Published in: US.

Yang, S., et al., "A microfluidic device for continuous, real time blood plasma separation", "Lab on a Chip article downloaded Feb. 2, 2011 from http://pubs.rsc.org", Apr. 19, 2006, pp. 871-880, vol. 2006, No. 6, Publisher: The Royal Soc'y of Chem., Published in: US.

Zhang, J., et al., "A lab-on-CD prototype for high-speed blood separation", "J. of Micromech. Microeng. article downloaded Sep. 8, 2011 from http://iopscience.iop.org", Nov. 19, 2008, pp. 1-6, vol. 2008, No. 18, Publisher: IOP Publishing, Published in: GB.

Turu, Takeshi, "Japanese Office Action re Application No. 2013558201", dated Apr. 5, 2016, p. 8, Published in: JP.

Hara, Daiki, "Japanese Office Action Re Application No. 2013-558201", dated Dec. 6, 2016, p. 6, Published in: JP.

\* cited by examiner

SYSTEMS AND METHODS FOR AUTOLOGOUS BIOLOGICAL THERAPEUTICS

FIELD OF THE INVENTION

This application is a continuation of U.S. application Ser. No. 13/421,728 filed Mar. 15, 2012 and entitled "SYSTEMS FOR AUTOLOGOUS BIOLOGICAL THERAPEUTICS," which claims priority to U.S. Patent Application Ser. No. 61/453,658, filed Mar. 17, 2011 and entitled "SYSTEMS AND METHODS FOR PRODUCING A PLATELET RICH PLASMA," all of which is incorporated herein by reference in its entirety and for all purposes.

FIELD OF THE INVENTION

The present invention relates to systems, methods, and apparatuses for autologous biological therapeutics, including but not limited to platelet rich plasma (PRP) and bone marrow cell concentrate (BMCC) therapy and technology.

BACKGROUND OF THE INVENTION

One of the proven methods of enhancing hard and soft tissue regeneration is the addition of human growth factors to a wound site or surgical incision. A safe and simple way of procuring compatible growth factors in a clinical situation is by the isolation of platelets from the blood of the patient, referred to as an "autologous platelet concentrate."

Platelets are blood cells primarily involved in arresting bleeding. However, they also contain proteins called growth factors that help promote healing and tissue regeneration. Man-made highly concentrated mixtures of platelets (platelet concentrates or Platelet rich plasma (PRP)) have higher platelet counts than natural blood and have been found to stimulate the body's soft tissue and hard tissue regeneration.

Bone marrow cell concentrate (BMCC) may include a number of target cells including the following: stem-like cells (pluripotent cells) (e.g., monocytes), white blood cells, platelets, neutrophils, lymphocytes, eosinophils, and basophils, all of which have a variety of uses in healing, regeneration, and treatment. Since it is difficult to separate any one or more of these cell fractions from a BMCC, they are typically all inserted or injected into a patient. In one embodiment, the BMCC includes platelets and white blood cells, including a stem cell fraction, where the stem cell fraction enhances the regenerative effects of the platelets.

Improved understanding of the role of growth factors as biochemical mediators of wound healing has paved the way for a new family of bioactive therapeutic products to expedite wound healing. Delivery of growth factors (recombinant or as autologous platelets) has emerged as a possible commercial opportunity for improving the clinical outcomes of soft, bone, and connective tissue repair. However, there is inability in the art to control or manipulate final product concentrations to a narrow target range, required to study or define dose-response relationships, and ultimately validate therapeutic effectiveness of these agents.

While hemoanalysis machines are capable of measuring typical platelet concentrations, they are not suitable for measuring the high platelet concentrations found in PRP transfusions. These machines are also large and expensive (e.g., $15,000-20,000/unit).

Another challenge of forming platelet and BMC concentrations is that separation and concentration procedures can prematurely activate platelets thus starting the clotting cascade. Thus, there is a need for separation procedures that avoid premature activation of platelets.

SUMMARY

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

In one aspect, this disclosure describes a cell concentrating system. The system has a blood separation component, a first vessel, a second vessel, a first valve, a second valve, and a concentration and flow logic and control component. The blood separation component has a blood sample input and a centrifuge to separate the blood sample into a red blood cell fraction and a plasma fraction. The plasma fraction has a target cell-rich fraction and a target cell-poor fraction. The blood sample has a volume of between 60 mL and no more than 250 mL. The first vessel is for storing the target cell-poor fraction separated from the blood sample. The second vessel is for storing the target cell-rich fraction separated from the blood sample. The first valve is upstream of the first vessel and the second vessel, and downstream of the blood separation component. The second valve is for providing selective fluid communication between the first vessel and the second vessel. The concentration and flow logic and control component is configured to: control the first valve to remove the target cell-poor fraction to the first vessel and to remove the target cell-rich fraction to the second vessel; determine a first volume of the target cell-poor fraction in the first vessel to mix with the target cell-rich fraction in the second vessel in order to form a target cell-rich concentrate having a concentration of target cells that is within a target concentration range for studying or defining a dose-response relationship in a patient; determine whether the target cell-rich concentrate has a concentration of target cells within the target concentration range; and control the second valve to transfer the first volume of the target cell-rich fraction from the first vessel to the second vessel to form the target cell-rich concentrate. The target concentration range is between 1.0 and $1.5 \times 10^6$ target cells/$\mu$L, and the cell concentrating system is autologous.

In another aspect, a method of generating a target cell-rich concentrate is disclosed. The method includes obtaining a target blood sample having a volume of between 60 mL and 250 mL, and inputting the target blood sample into a cell concentration system. The method also includes causing the cell concentration system to: separate the target blood sample into a red blood cell fraction, a target cell-poor fraction, and a target cell-rich fraction; remove the target cell-poor fraction to a first vessel; remove the target cell-rich fraction to a second vessel in selective fluid communication with the first vessel; determine a first volume of the target cell-poor fraction in the first vessel to mix with the target cell-rich fraction in the second vessel in order to form a target cell-rich concentrate having a concentration of target cells that is within a target concentration range for studying or defining a dose-response relationship in a patient; determine whether the target cell-rich concentrate has a concentration of target cells within the target concentration range; and transfer the first volume of the target cell-rich fraction from the first vessel to the second vessel to form the target cell-rich concentrate. The target concentration range is between 1.0 and 1.5×106 target cells/μL. The target cell-rich concentrate is an autologous target cell-rich concentrate of the target blood sample.

In another aspect, a method of autologous therapeutics is disclosed. The method includes: extracting a target blood sample from a patient, the target blood sample having a volume of between 60 mL and 250 mL, and inputting the target blood sample into a cell concentration system. The method also includes causing the cell concentration system to: separate the target blood sample into a red blood cell fraction, a target cell-poor fraction, and a target cell-rich fraction; remove the target cell-poor fraction to a first vessel; remove the target cell-rich fraction to a second vessel in selective fluid communication with the first vessel; determine a first volume of the target cell-poor fraction in the first vessel to mix with the target cell-rich fraction in the second vessel in order to form a target cell-rich concentrate having a concentration of target cells that is within a target concentration range for studying or defining a dose-response relationship in a patient; determine whether the target cell-rich concentrate has a concentration of target cells within the target concentration range; and transfer the first volume of the target cell-rich fraction from the first vessel to the second vessel to form the target cell-rich concentrate. The target concentration range is between 1.0 and 1.5×106 target cells/μL. The target cell-rich concentrate is an autologous target cell-rich concentrate of the target blood sample. The method also includes injecting the autologous target cell-rich concentrate into the patient.

BRIEF DESCRIPTION OF THE DRAWINGS

Various objects and advantages and a more complete understanding of the present invention are apparent and more readily appreciated by referring to the following detailed description and to the appended claims when taken in conjunction with the accompanying drawings:

DETAILED DESCRIPTION

Figure 1:
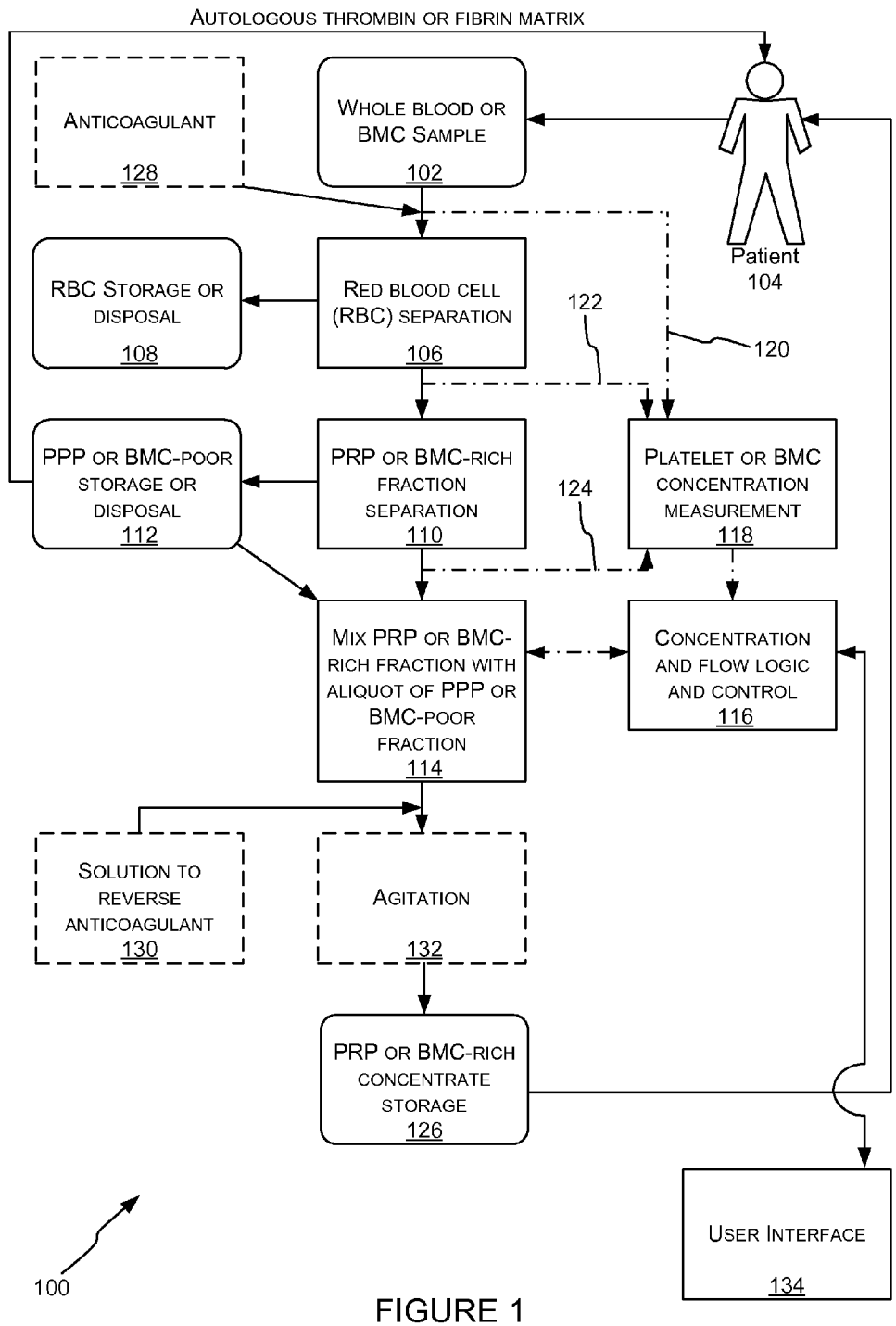
FIG. 1 illustrates a flow diagram of operations and components of a system for autologous infusion of platelet-rich plasma concentrates or bone marrow cell concentrates having specified concentration ranges.

There is a long-felt need in the art for systems, methods, and apparatus capable of generating narrow concentration ranges of PRP and BMCC. With such well-known concentrations, clinical studies of the effects of different concentrations on patients will be greatly improved.

For the purposes of this disclosure, bone marrow cells (BMCs) and bone marrow cell concentrates (BMCCs) include, but are not limited to, any one or more of the following: stem-like cells (pluripotent cells) (e.g., monocytes), white blood cells, platelets, neutrophils, lymphocytes, eosinophils, and basophils. In fact, BMCs include any cells found in a bone marrow sample and a BMCC includes any of the cells found in a bone marrow sample, but at higher-than-natural concentrations. Throughout this disclosure, a BMC-rich fraction refers to a substance or fluid having an increased concentration of any one or more target or desired cells as compared to the natural concentration in a human body. A BMC-poor fraction refers to a substance or fluid having a decreased concentration of any one or more target or desired cells as compared to the natural concentration in a human body.

The concentrates of this disclosure can comprise one or more of cells, signals, and scaffolds. These components can be harvested and generated from many sources. For instance, in an autologous system, the patient is treated using components removed from the same patient.

For the purposes of this disclosure, "cells" include mesenchymal stem cells (MSCs) originating from bone marrow, fat, blood, synovium, or other tissues. Cells also include pluripotent cells from bone marrow, blood, and other sources. Cells further include native tissue cells, which can be stimulated to grow and proliferate via signals.

For the purposes of this disclosure, "signals" refer to human growth factor proteins, and can be derived from platelets or from autocrine (cell-cell) sources. Additionally, for the purposes of this disclosure, "scaffolds" refer to a mechanical matrix made from a blood-based fibrin that can be used to deliver and provide a platform for tissue growth in vivo. As herein disclosed, there is often a blood based fibrin that creates a scaffold by inducing a clotting cascade in the blood, converts fibrinogen to fibrin, and creates a mechanical fibrin matrix. Cells and/or growth factor proteins can be implanted or 'seeded' into a scaffold where the scaffold supports three-dimensional tissue formation from the seed.

Whole blood is human blood from a standard blood donation. Whole blood can be combined with an anticoagulant during a collection process, but is generally otherwise unprocessed. The capitalized "Whole Blood" means a specific standardized product for transfusion or further processing. The lower case "whole blood" encompasses any unmodified collected blood.

Flow cytometry (FCM) is a technique for counting and examining microscopic particles, such as cells and chromosomes, by suspending them in a stream of fluid and passing them by an electronic detection apparatus. It allows simultaneous multiparametric analysis of the physical and/or chemical characteristics of up to thousands of particles per second.

For the purposes of this disclosure, separation means chemically separating components, but not necessarily physical separation. For instance, centrifugation separates a fluid into layers that are primarily isolated from each other based on particle mass. However, there may be some overlap between the layers, and such is included in this disclosure's use of the term separation. At the same time, if those layers were then split into different vessels, this would also be considered separation.

FIG. 1 illustrates a flow diagram of operations and components of a system for autologous infusion of platelet-rich plasma concentrates or bone marrow cell concentrates having specified concentration ranges. FIG. 1 will be described in conjunction with FIGS. 2-4, which describe methods of the same. A whole blood sample or bone marrow cell (BMC) sample 102 is taken from a patient 104 (Blocks 202, 302, 402, 502, 602, 702). The sample 102 enters a red blood cell (RBC) separation component 106 (first separation component), which separates RBCs from a plasma fraction of the sample 102 (Blocks 204, 304, 404, 504, 604, 704). The RBCs can be stored in an RBC storage or disposal vessel 108 (Blocks 206, 306, 406, 506, 606, 706).

The plasma fraction can then be separated in a PRP or BMC fraction separation component 110 (second separation component). The second separation component 110 separates the plasma fraction into a platelet-poor plasma (PPP) fraction and a platelet-rich plasma (PRP) fraction, or a BMC-poor fraction and a BMC-rich fraction (Blocks 210, 310, 410, 510, 610, 710). The PPP or BMC-poor fraction can be stored in a PPP or BMC-poor storage or disposal vessel 112.

The PRP or BMC-rich fraction can be mixed with an aliquot of the PPP or BMC-poor fraction in a mix component 114 (Blocks 212, 312, 412, 512, 612, 712). Alternatively, rather than removing the entire PPP or BMC-poor fraction and then remixing an aliquot of the removed fraction, a first aliquot of the PPP or BMC-poor fraction can be removed to the PPP or BMC-poor storage or disposal vessel 112, while a second aliquot is left with the PRP or BMC-rich fraction.

The mix component 114 can be controlled by a concentration and flow logic and control 116. The concentration and flow logic and control 116 determines a volume of the aliquot to be added to the PRP or BMC-rich fraction based on a determination of the total number of platelets or BMCs that were in the whole blood sample or BMC sample 102 (Blocks 208, 308, 408, 508, 608, 708). Such determination can be made by measuring a platelet or BMC concentration 120, 122, 124, at various points in the process via a platelet or BMC concentration measurement component 118. For instance, concentration 120 can be measured from the whole blood or BMC sample (Blocks 408, 708). Concentration 122 can be measured after the RBC separation, thus measuring the platelet or BMC concentration in a plasma (Blocks 208, 508). As another alternative, a concentration 124 can be measured after the PRP or BMC-rich fraction has been separated in second separation component 110 (Blocks 308, 608). This concentration 124 is measured from the PRP or BMC-rich fraction. All three concentrations 120, 122, 124 should be identical measurements, although they may vary since the separations are not ideal and thus some platelets or BMC may end up in the RBC fraction or the PPP or BMC-poor fraction. Since platelets and bone marrow cells can separate, an agitation step may be added before any of the first, second, or third concentrations 120, 122, 124 are measured.

The concentrations 120, 122, 124 can be multiplied by the sample 102 volume, the plasma volume, or the PRP or BMC-rich fraction volume, respectively, to determine a total number of platelets or BMCs in the PRP or BMC-rich fraction. The concentration and flow logic and control 116 divides this total number by a target concentration (e.g., $0.8$-$2.0 \times 10^6$ platelets/μL or $1.0$-$1.5 \times 10^6$ platelets/μL) to get a total target volume that the mix should attain. The amount of PPP or BMC-poor fraction to mix with the PRP or BMC-rich fraction is the difference between the total target volume and the volume of the PRP or BMC-rich fraction (for a further explanation, see Equations (1)-(6)).

The mixture of the aliquot of PPP or the aliquot of the BMC-poor fraction and the PRP or BMC-rich fraction can be stored in a PRP or BMC-rich concentrate storage vessel 126. This mixture can also be referred to as an PRP or BMC-rich concentrate and can have a target concentration of platelets or BMCs and/or a target volume. The PRP or BMC-rich concentrate is then available for infusion back into the patient 104 (Blocks 216, 316, 416, 516, 616, 716). The PRP or BMC concentrate can be compatible with blood bank cross-matched blood.

In one alternative, an optional anticoagulant 128 can be added to the whole blood sample or BMC sample 102 before the first separation in order to help prevent the platelets from activating (Blocks 222, 322, 422, 522, 622, 722). Similarly, a solution 130 to reverse the anticoagulant 128 can be added to the PRP or BMC-rich concentrate before or after the concentrate has reached the PRP or BMC-rich concentrate storage vessel 126.

Another embodiment can optionally agitate the concentrate before or after the concentrate reaches the PRP or BMC-rich storage vessel 126 via an agitation component 132. This agitation can help mix the concentrate and/or begin activation of the platelets in the concentrate. The agitation component 132 can be separate from or integrated with the PRP or BMC-rich concentrate storage vessel 126. Agitation can involve stirring in one embodiment.

A user interface 134 can be used to interface with, control, and monitor the process via the concentration and flow logic and control 116. The user interface 134 can enable a user (e.g., a doctor, nurse, or technician) to monitor parameters of the procedure as well as to provide inputs such as a target concentration and/or a target volume of the PRP or BMC-rich concentrate.

In one embodiment, another measurement and analysis of the PRP or BMC concentration of the concentrate is performed before infusion into the patient 104 (Blocks 214, 314, 414, 514, 614, 714). If the concentrate falls within a target range of concentrations, then the concentrate can be provided to the patient 104 (Blocks 216, 316, 416, 516, 616, 716). However, if the concentration does not fall within the target range, then the concentrate can be remixed with the RBC fraction (Blocks 218, 318, 418, 518, 618, 718) and passed back through the process starting with the RBC separation (Blocks 204, 304, 404, 504, 604, 704), until the PRP or BMC-rich concentrate falls within the target range. Where the determination of platelet or BMC concentration 120 was made from the sample 102 (Blocks 408, 708), there may be an optional determination of total platelets (Block 424) or total number of BMCs (Block 724) before the first separation (Blocks 404, 704).

In an embodiment an optional anticoagulant 128, such as ACDA, can be added to the whole blood or BMC sample 102 before any separating procedures begin. Since the separation procedure as well as the mere movement of the platelets between vessels, centrifuges, or any other components of the system entail agitation of the platelets, and agitation can initiate undesired activation (clotting) of the platelets, the anticoagulant 128 helps to preserve the platelets in a non-activated state until they are ready to be infused back into the patient 104. In one embodiment, 3 mL of anticoagulant can be added to 50 mL of whole blood or 5 mL of anticoagulant added to 50 mL of BMC. In the case of a BMC sample 102, an aspiration syringe can be flushed before the BMC sample 102 is passed to the separation component 106. For instance, an aspiration syringe can be flushed with heparin (e.g., 1,000 U/mL).

In one embodiment, a whole blood or BMC sample 102 is between 60-250 mL, while in another the sample 102 is between 60-120 mL. The Whole Blood can be sourced from an intravenous catheter. The BMC can be harvested by needle aspiration from an intramedullary cavity of the anterior or posterior hip, shoulder, or knee, although other methods and sources for acquiring BMC are also envisioned.

While the presently discussed systems and methods describe autologous systems and methods (infusion back into the source patient 104), in other embodiments, the source patient and the patient to be infused can be different.

A BMC sample 102 may be put through an initial removal stage for removing high molecular weight components such as bone particulates. The BMC sample 102 can then be filtered to remove any remaining fat and/or large particles (Blocks 526, 626, 726). A 170-260 µm filter can be used in one instance.

The red blood cell (RBC) separation component 106 separates the sample 102 into an RBC fraction and a non-RBC fraction or plasma fraction. In the case of a whole blood sample 102, the non-RBC fraction may include nucleated or white blood cells (WBCs), platelets, and serum. In the case of a BMC sample 102, the non-RBC fraction can include plasma, platelets, and WBCs (including pluripotent cells).

The RBC separation component 106 can carry out a 'soft spin' via centrifuge in one embodiment. In one embodiment, the soft spin can involve centrifugation at 2500-3000 RPM for 8-15 minutes where whole blood is involved, and 2400 RPM for 10 minutes where BMCs are the source, although these exemplary specifications are not limiting. In centrifugation, the plasma fraction is the fraction of the sample 102 that accumulates above the RBC fraction or closer to a center of the centrifuge (RBCs are the heaviest components of an RBC sample). The RBCs accumulate below the plasma fraction since they tend to be heavier. Within the plasma fraction, the centrifugation may also cause further separation between mainly plasma particles and a "buffy coat," which may include nucleated cells, platelets, plasma, and WBCs. The buffy coat tends to be found between the plasma and the RBC fraction.

The RBC separation component 106 can alternatively use a variety of other separating components and methods including, but not limited to, separation according to microfluidic channel separation, polymer-based separation, acoustophoresis, various lab-on-chip or lab-on-CD (compact disc) technologies, flow cytometry, dielectrophoresis, laser impedance, flow cytometry, and use of fluorescent or other markers. Microfluidic channel separation involves passing a fluid through channels of varying diameters such that particles of varying sizes can only fit through certain channels, and thus particles can be separated depending on which channels they are able to pass through. Acoustophoresis involves the use of acoustic signals to separate components of a fluid. The polymer-based method involves adding a polymer to the plasma fraction that causes platelets to separate from the plasma. The RBC separation component 106 should be selected so as to minimize platelet activation and maximize platelet yield.

The RBC fraction can be directed to an RBC storage vessel 108 for later transfusion or disposal via a valve or pump. The plasma fraction can be directed to a different vessel or a portion of the system where further separation is to occur. In some embodiments, the RBC fraction can remain in the first separation component 106 after the plasma fraction has been removed, and since the first separation component 106 may be disposable, the RBC fraction can be left in the first separation component 106 for disposal. In such an embodiment, a separate RBC storage or disposal vessel 108 is not implemented.

In the case of a plasma fraction derived from bone marrow, a filtration process can be used to further filter the plasma (e.g., a ~200 µm mesh filter). For instance, any anti-coagulated flushed syringe can be used to pull the plasma fraction through a filter.

Once the RBC fraction is separated from the plasma fraction, the plasma can pass to the plasma-rich platelet (PRP) or the BMC-rich fraction separation component 110 (the second separation component). The second separation component 110 separates the plasma into a platelet-poor plasma (PPP) fraction and a platelet-rich plasma (PRP) fraction or a BMC-poor fraction and a BMC-rich fraction. In many cases, the PPP fraction or the BMC-poor fraction are the larger fractions. The PPP fraction tends to have a low or negligible concentration of platelets.

In some embodiments, the second separation component 110 is the RBC separation component 106 (also known as a first separation component) and will hereinafter be referred to as the separation component 106/110. For instance, a single centrifuge can be used to separate the sample 102 into an RBC fraction, a PRP or BMC-rich fraction, and a PPP or BMC-poor fraction. This can involve first removing the plasma fraction from the separation component 106/110 and then passing the plasma fraction back into the separation component 106/110 or leaving the plasma fraction in the separation component 106/110 while the RBC fraction is first separated and removed, and then the plasma fraction is separated. Alternatively, the three fractions can be simultaneously separated.

In other embodiments, the first separation component 106 and the second separation component 110 are separate and different components. For instance, two centrifuges may be used. However, the first and second separation components 106, 110 can also be different types of components. In one case, a centrifuge can be used as the first separation component 106 and a set of microfluidic pores of different diameter can be used as the second separation component 110. Many other variations are also possible.

Where the second separation component 110 is a centrifuge, or where both separation components 106, 110 are the same centrifuge, a second or 'hard spin' can be performed on the plasma fraction. The hard spin can involve a 2800-3200 RPM spin for 5-8 minutes where whole blood is the source and 3400 RPM for 6 minutes where BMCs are the source, although these exemplary parameters are not limiting. The hard spin separates the plasma into a PPP fraction and a PRP fraction, or a BMC-poor fraction and a BMC-rich fraction, where the PPP fraction or the BMC-poor fraction tends to be a larger upper layer comprising lighter particles and only a small concentration of platelets or BMCs. Underneath this layer is a smaller "buffy coat" or "pellet" comprising the heavier platelets or BMCs, which accumulate towards an outer radius of the centrifuge.

The PRP or BMC-rich fraction separation component 106 can alternatively use a variety of other separating components and methods including, but not limited to, separation according to microfluidic channel separation, polymer-based separation, acoustophoresis, various lab-on-chip or lab-on-CD (compact disc) technologies, flow cytometry, dielectrophoresis, laser impedance, flow cytometry, and use of fluorescent or other markers.

Once the plasma fraction is separated, the PPP or BMC-poor fraction can be directed to a PPP or BMC-poor storage or disposal vessel 112. For instance, one or more valves and pumps can be used to direct the fluid flow.

In one embodiment, rather than remove the PPP or BMC-poor fraction, only an aliquot of this fraction is removed to the storage or disposal vessel 112. Selection of the volume of this aliquot will be discussed later relative to the concentration and flow logic and control 116 and the mix component 114.

The mix component 114 can agitate the mixture of PRP and PPP or BMC-rich and BMC-poor in order to suspend cells within the fluid. Alternatively, the mere action of forcing the two substances into the same vessel can achieve satisfactory mixing.

The volume of the aliquot of PPP or BMC-poor plasma fraction to mix with the PRP or BMC-rich plasma fraction in order to achieve the target concentration is determined as follows. For readability, this description will refer only to platelets, but is equally applicable to BMCs. First a total number of platelets, $P_{total}$, in the sample 102 is determined. This is done by: (a) measuring or estimating a platelet concentration, $PC_0$, (e.g., platelet concentrations 120, 122, 124) and (b) multiplying the platelet concentration, $PC_0$, by a volume, $V_0$, of the fluid in which the platelet concentration was measured in. This is shown in Equation (1) as follows:

$$P_{total} = PC_0 \times V_0 \quad (1)$$

There are at least three locations or times during the process where the concentration $PC_0$ and the volume $V_0$ can be determined. First, the first concentration 120 can be measured from the whole blood sample 102. Second, the second concentration 122 can be measured after the first separation component 106 has separated the sample 102 into a RBC fraction and a plasma fraction. The second concentration 122 can be measured either before or after the RBC fraction has been moved to the RBC storage or disposal vessel 108. Either way, the second concentration 122 is taken from the plasma fraction not from the RBC fraction. Third, the third concentration 124 can be measured after the plasma fraction is separated into an RBC fraction and a PPP fraction.

The concentration $PC_0$ is passed to the concentration and flow logic and control 116 where it is used to determine a total number of platelets in the volume $V_0$ of fluid that was measured. The platelet or BMC concentration measurement component 118 can also measure the volume $V_0$ (e.g., via a flow meter) in which the concentration $PC_0$ was measured. Alternatively, the concentration $PC_0$ can be measured within a space having a known volume $V_0$. For instance, the sample 102, or the plasma fraction, or the PRP can have known volumes. In another embodiment, a user (e.g., a doctor, nurse, or technician) can enter the volume $V_0$ into the user interface 134, which provides the volume $V_0$ to the concentration and flow logic and control 116. Thus, the concentration and flow logic and control 116 can utilize both the concentration $PC_0$ and the volume $V_0$ of the fluid measured to solve for the total number of platelets PTOTAL according to Equation (1).

To achieve a target (e.g., user-defined) PRP concentration, $PC_t$, some aliquot of the PPP fraction is mixed with the PRP fraction. An exemplary range of target PRP concentrations, $PC_t$, is $0.8-2.0 \times 10^6$ platelets/µL or $1.0-1.5 \times 10^6$ platelets/µL. An exemplary target PRP concentration, $PC_t$, is $1.5 \times 10^6$ platelets/µL. In one embodiment this involves removing some of the PPP fraction then mixing the remaining PPP fraction and the PRP fraction. In another embodiment, the PPP fraction is removed, and then a portion of the PPP fraction is mixed back in with the PRP fraction. In both cases, knowing how much of the PPP fraction to mix with the PRP fraction can be determined by calculating a target volume for the mixture $V_T$. This value is given as follows:

$$V_t = \frac{P_{total}}{PC_t} \quad (2)$$

The target volume, $V_t$, is equal to the number of platelets, $P_{total}$, divided by the target PRP concentration $PC_t$. Equation (2) can be simplified by substituting Equation (1) for $P_{total}$ in Equation (2) as follows:

$$V_t = \frac{PC_0 \times V_0}{PC_t} \quad (3)$$

To achieve the target PRP concentration $PC_t$ an aliquot $V_{PPP}$ of the PPP fraction is mixed with the PRP fraction, having a volume $V_{PRP}$ (measured by a flow meter, for example), so that the combination equals the target volume $V_t$. This can be written as Equation (4) and solved for the aliquot $V_{PPP}$ in Equations (5) and (6) as follows:

$$V_t = V_{PPP} + V_{PRP} \quad (4)$$

$$V_{PPP} + V_{PRP} = \frac{PC_0 \times V_0}{PC_t} \quad (5)$$

$$V_{PPP} = \frac{PC_0 \times V_0}{PC_t} - V_{PRP} \quad (6)$$

Thus, where a portion of the PPP fraction is removed, some of the PPP fraction is removed until the volume of the remaining PPP fraction and the PRP fraction equals $V_t$. Said another way, a portion of the PPP fraction is removed until the remaining PPP fraction has a volume equal to $V_{PPP}$ as in Equation (6). Where the entire PPP fraction is removed, and then an aliquot having volume $V_{PPP}$ is added back with the PRP fraction, $V_{PRP}$, the aliquot of the PPP fraction can be selected so that the combined volume of the aliquot of the PPP fraction, $V_{PPP}$, and the volume of the PRP fraction, $V_{PRP}$, equals the target volume $V_t$.

Equation (6) may suffer from the fact that some platelets are removed with the RBC by the first separation component 106, and with the PPP fraction by the second separation component 110, however such numbers can be considered negligible when the separations are carried out with care.

As noted earlier, the derivation of Equation (6) was described relative to PRP, but is equally applicable to BMC-rich plasma. In particular, Equation (7) shows Equation (6) as applied where bone marrow is the source and a BMC-rich plasma concentrate is the end goal.

$$V_{BMC-} = \frac{BMCC_0 \times V_0}{BMCC_t} - V_{BMC+} \qquad (7)$$

The concentration of the BMCs, $BMCC_0$, can be measured from the BMC sample 102, after the first separation component 106 has separated the BMC sample 102 into an RBC fraction and a plasma fraction, or after the second separation component 110 has separated the plasma fraction into a BMC-poor fraction and a BMC-rich fraction. The target concentration of BMCs is $BMCC_t$. The volume of the BMC-rich fraction is $V_{BMC+}$, and the volume of the aliquot of the BMC-poor fraction to be mixed with the BMC-rich fraction is $V_{BMC-}$. Once again, the aliquot of the BMC-poor fraction, $V_{BMC-}$, can be added to the BMC-rich fraction or left with the BMC-rich fraction as the rest of the BMC-poor fraction is removed. Equations (6) and (7) can also be adapted for use with any target blood cells such as white blood cells (e.g., monocytes), platelets, bone marrow cells, and "stem-like" or "pluripotent" cells.

During this process, the concentration and flow logic and control 116 can provide instructions to a human user via the user interface 134 indicating how much of the PPP or BMC-poor fraction to mix with the PRP or BMC-rich fraction. Alternatively, the concentration and flow logic and control 116 can provide a value for the target volume $V_t$ to a user via the user interface 134. In another embodiment, the concentration and flow logic and control 116 can automatically control the mix component 114 and control the volume of the PPP or BMC-poor fraction that is mixed with the PRP or BMC-rich fraction. For instance, the concentration and flow logic and control 116 can control a valve and pump that either removes a certain amount of the PPP fraction or adds a certain amount of the PPP fraction back in with the PRP or BMC-rich fraction.

The user interface 134 can display information describing the measurements that the platelet or BMC concentration measurement component 118 is performing. The user interface 134 can be part of or separate from the concentration and flow logic and control 116. This information can also be stored in a memory or transferred through telemetry to a central record keeping system.

The user interface 134 can also be used by a user (e.g., doctor, nurse, or technician) to set a target PRP or BMC concentration $PC_t$ or $BMCC_t$ and a target volume $V_t$. The user interface 134 can also be used to request and display results from a concentration analysis of the PRP or BMC-rich concentrate. Such analysis can be performed after the concentrate has been formed, but before the concentrate is administered to a patient, to ensure that the desired concentration was created.

The platelet or BMC concentration measurement component 118 can include a variety of hemoanalysis machines and methods. For instance, fluorescent activated cell sorting (FACS) can determine the concentration of a specific pluripotent, stem-like cell, within a fluid based on antibody cell surface markers. Other exemplary embodiments of the concentration measurement component 118 include those for optical microscopy, optical light scattering, and electrical impedance. Optical microscopy involves a computer-controlled pattern and shape recognition component and logic that counts and differentiates particles by shape and size. In some instances, this method cannot be performed continuously, and may therefore require sampling of discrete portions of a fluid. In one embodiment, sampling of a thin fluid layer may be implemented. Optical light scattering may use a hydrodynamic focused stream of fluid and the method can count different types of cells and molecules especially where fluorescence markers or anti-bodies are used. Electrical impedance may use a hydrodynamic focused steam of fluid.

In some embodiments, either of these concentration measurement components 118 can be combined with a particle separation component. For instance, a microfluidic channel device could be used to separate particles within a PRP fraction, while a light scattering device measures a number of particles in each fluid stream. The combination of a particle separation device and a particle counting device can be beneficial where the particle counting device is not able to distinguish between different types of cells or particles within the same stream.

In one embodiment, hemoanalysis can be performed on the PRP or BMC-rich concentrate (Blocks 214, 314, 414, 514, 614, 714). This hemoanlaysis can be in addition to or in the alternative to one or more previous hemoanalysis steps. For instance, in one embodiment, hemoanalysis can be performed on the whole blood sample or BMC sample and on the concentrate. In another embodiment, hemoanalysis can be performed after the first separation as well as on the concentrate.

In an embodiment, autologous thrombin or a fibrin matrix can be prepared from some or all of the PPP or BMC-poor fraction in the PPP or BMC-poor storage or disposal vessel 112 (Blocks 220, 320, 420, 520, 620, 720). The effects of the anticoagulant 128 can be reversed, for example, by addition of CaCl (e.g., a 10% solution of CaCl can be added to the PPP or BMC-poor fraction). The PPP or BMC-poor fraction and whatever substance is used to reverse the anticoagulant 128 can be agitated (e.g., for approximately 1 minute) resulting in formation of a fibrin clot. During or after clot formation, additional PPP or some of the BMC-poor fraction can be added to the mixture. Further agitation can be performed and the mixture can be given time for the clot to continue to form. When clotting is complete, the clot can be removed and manually compressed (or re-centrifuged to compress).

In the case of autologous thrombin formation, prothrombin protein is cleaved in the process of reversing the anticoagulant and thrombin is produced. Removal of the clot leaves serum and a low concentration of thrombin. The thrombin can be combined with implanted PRP to initiate and regulate a release of platelet growth factors to stimulate regenerative responses.

Where fibrinogen in PPP is activated by calcium reversal of the anticoagulant or the addition of the autologous thrombin to induce cleavage of the fibrinogen to fibrin, a fibrin matrix or scaffold is formed. The matrix or scaffold can be implanted to act as a scaffold from which native or implanted cells can attach and proliferate to form new tissue.

The clot can be transferred to an implantation destination in the patient 104. The implantation destination can be a joint or area where regeneration is desired, or any other selected site in the patient 104. After the clot is removed, the remaining PPP or BMC-poor can be used to improve platelet activation by combination with the PRP or BMC-rich concentrate either in-vitro (creating a PRP membrane) or invivo (creating an activated PRP). Although the thrombin or fibrin matrix can be autologously applied, they can also be implanted into another patient other than the patient 104.

The autologous thrombin or fibrin matrix can be removed via syringe and implanted into the patient 104. In one alternative, a fibrin matrix or Autologous Platelet Gel (APG) can be autonomously created from activated PPP and a portion of the PRP concentrate. Other products include activated PPP containing autologous thrombin. The manual or autonomous procedures can be carried out in the operating room or desired treatment location.

PPP can include an acellular blood fraction comprising ~55% of blood volume, 91% water content, and residual proteins. Although PPP is preferably devoid of platelets, in practice a small residual platelet fraction may be observed.

In some embodiments, the platelet or BMC concentration measurement component 118 can also measure other blood component concentrations such as white blood cell concentration. Other concentrations that can be measured include those for red blood cells, Neutrophils, Lymphocytes, Monocytes, Eosinophils, and Basophils. These alternative measurements can be used in embodiments, where concentrations of non-platelet and non-BMC blood cells are also being concentrated to a target concentration or target concentration range.

Sometimes the mixing of mix component 114 is not sufficient to suspend the platelets in the PRP or BMC concentrate. In these cases, or to enhance platelet activation, an optional agitation component 132 can agitate the PRP or BMC concentrate. Where BMCs are used, the pellet can be reconstituted (increased liquid content) in one of three mediums to ease infusion into the patient 104: accellular bone marrow aspirate; blood plasma; or PRP.

One or more of the first and second separation components 108, 110, the platelet or BMC concentration measurement component 118, the concentration and flow logic and control 116, and the mix component 114 can be discarded after use in order to enhance sterility within the system 300. All storage vessels 108, 112, 126 can also be disposable.

The system 100 can take a variety of forms including a miniaturized form such as a handheld or bench top system or other portable implementations. Portability can include being handheld, lightweight, and/or supported by a cart. The system 100 could also be designed so that continuous or intermittent infusions of PRP could be administered to a patient over a period of time. In an embodiment, the system 100 can be implemented wholly or partially as one or more microelectromechanical systems (MEMS) devices and/or as a lab on a chip.

The systems and methods herein disclosed can also achieve a number of further goals via various alternative embodiments. In an embodiment, blood product sterility is maintained, for instance via inclusion of one or more disposable components. In an embodiment, blood is collected from a patient prior to an operation and used to prepare a final PRP product for the operation. In an embodiment, a PRP membrane is created. Alternatively, activated PRP is used to create PRP within an autologous fibrin matrix. In another embodiment, the system 100 can create a PRP or BMC concentrate within 30 minutes.

The systems and methods can incorporate, or be incorporated into, existing technologies and components used in automated transfusion and hemoanalysis machines. In addition to counting, measuring and analyzing red blood cells, white blood cells, platelets, or other blood components, automated hematology analyzers can also measure the amount of hemoglobin or chemical regulators in the blood and within each red blood cell.

The systems and methods described herein can be applied to injured or pathologic tissue to stimulate and/or enhance repair or regeneration. Methods of implantation can include percutaneous (injection) or intra-operative (surgical) application. Other embodiments can include an implanted or partially implanted continuous or periodic delivery system for providing defined dosages over time.

Other sample sources that can be used in place of whole blood and bone marrow including fat, synovium, and other tissue.

Figure 2:
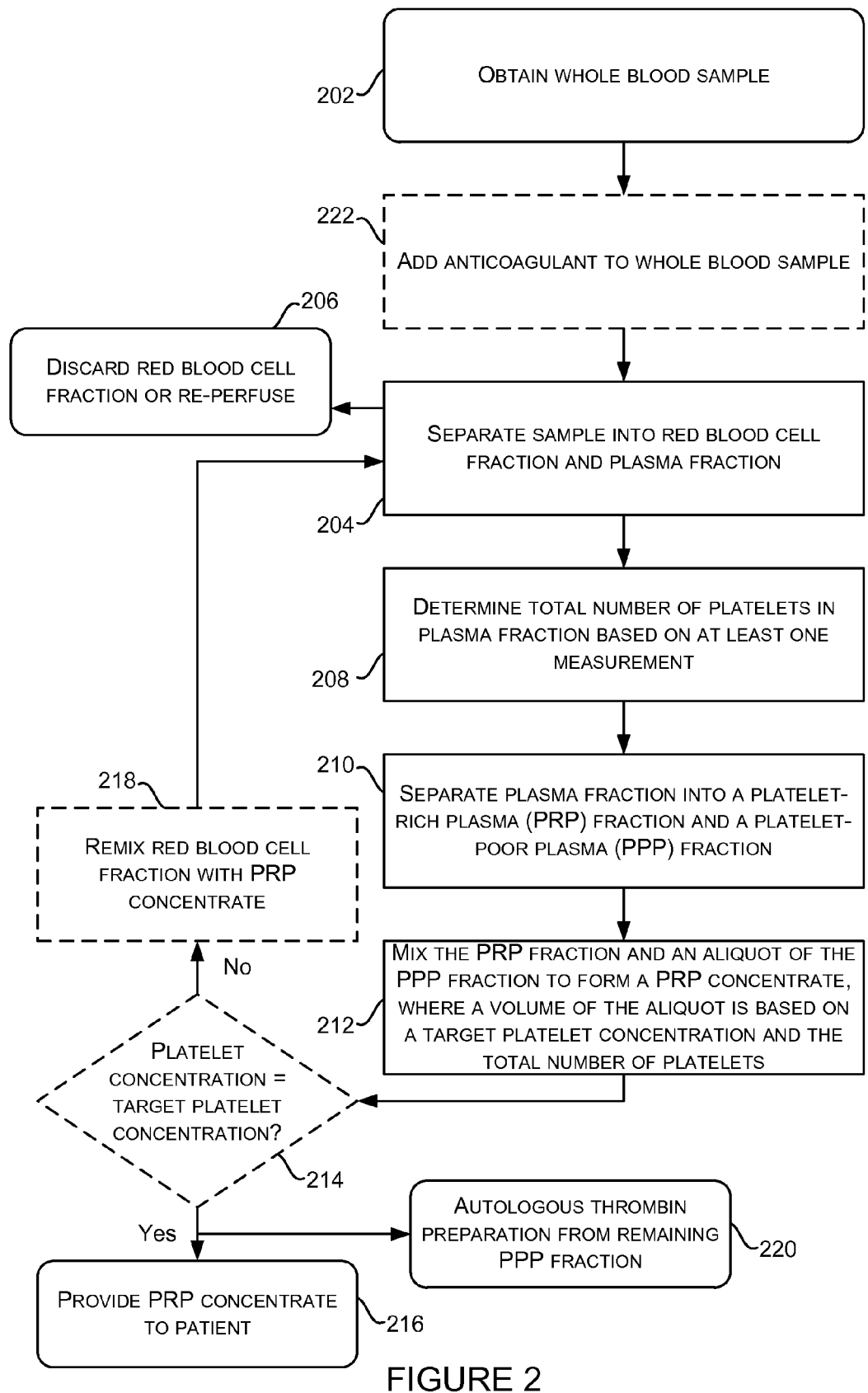
FIG. 2 illustrates a method for generating a PRP concentrate of a specific platelet concentration.

FIG. 2 illustrates a method for generating a PRP concentrate of a specific platelet concentration. The method 200 includes obtaining a whole blood sample in obtain sample operation 202 and optionally adding an anticoagulant in add anticoagulant operation 222. Then a first separation operation 204 separates the sample into a red blood cell (RBC) fraction and a plasma fraction. The RBC fraction can be discarded or re-perfused into a patient in a discard or re-perfuse operation 206.

The total number of platelets, $P_{total}$, in the plasma fraction can be determined in determine operation 208. This operation 208 utilizes at least one measurement such as a concentration measured by a hemoanalysis apparatus. The platelet concentration, $PC_0$, can be multiplied by a volume $V_0$ of the liquid, as measured by a flow meter for instance, from which the concentration measurement was made. The volume, $V_0$, times the concentration, $PC_0$, gives a total number of platelets, $P_{total}$. The plasma fraction is then separated further via second separation operation 210 (e.g., microfluidic channel separation or centrifugation), in which a platelet-rich plasma (PRP) fraction (high concentration of platelets) and a platelet-poor plasma (PPP) fraction (negligible platelet concentration) are generated.

The PRP fraction and an aliquot of the PPP fraction, $V_{PPP}$, are mixed in mix operation 212. The volume of the aliquot, $V_{PPP}$, can be based on a target platelet concentration, $PC_t$, and the total number of platelets, $P_{total}$ (e.g., Equation (6)). The mix operation 212 forms a PRP concentrate which can then be provided to a patient in provide PRP concentrate to patient operation 216. The remaining PPP fraction can also be used to form an autologous thrombin preparation for implantation into a patient in an autologous thrombin preparation operation 220.

Optionally, after the PRP concentrate is formed in mix operation 212, the platelet concentration can be checked to ensure that the platelet concentration falls within a target range (or within a margin of error of a target platelet concentration) in an optional decision 214. If the decision 214 finds that the PRP concentrate falls within the target range or within a margin of error of the target concentration, then the PRP concentrate can be provided to a patient. If not, then the concentrate can be remixed with the RBC fraction and the process can be repeated starting with the first separation operation 204.

Since settling may cause the concentrate to separate at least partially into a PPP layer and a PRP layer, an agitation operation may optionally be used to suspend the platelets prior to infusion.

Figure 3:
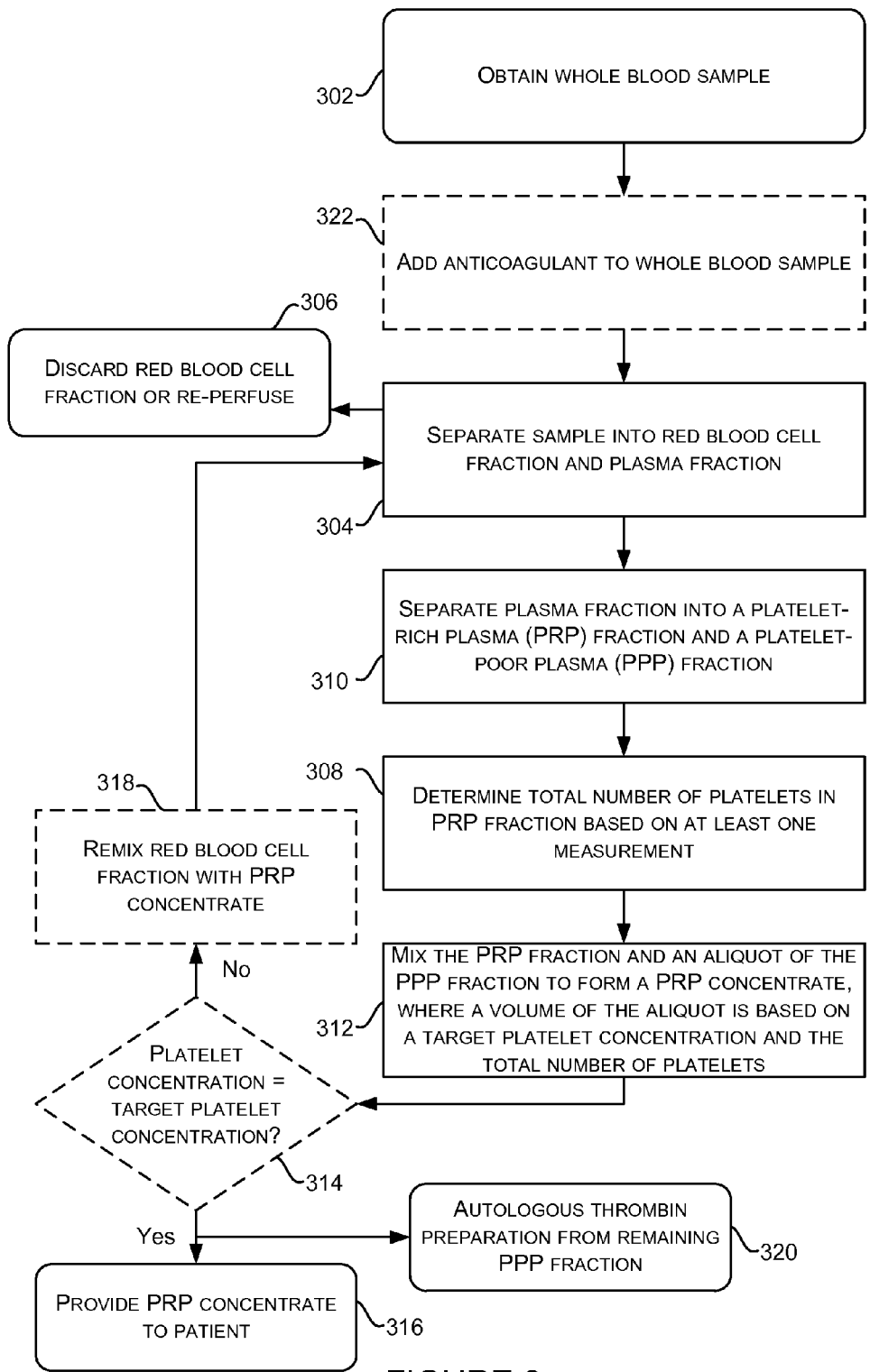
FIG. 3 illustrates another method for generating a PRP concentrate of a specific platelet concentration.

FIG. 3 illustrates another method for generating a PRP concentrate of a specific platelet concentration. The method 300 is nearly identical to the method 200 with the exception that the determine operation 308 takes place on the PRP fraction after the second separation operation 310, rather than between the first and second separation operations 304, 310. In some embodiments, the first and second separation operations 304, 310 can be performed in a single operation by a single separation component (e.g., a centrifuge that creates an RBC fraction, a PRP fraction, and a PPP fraction).

Figure 4:
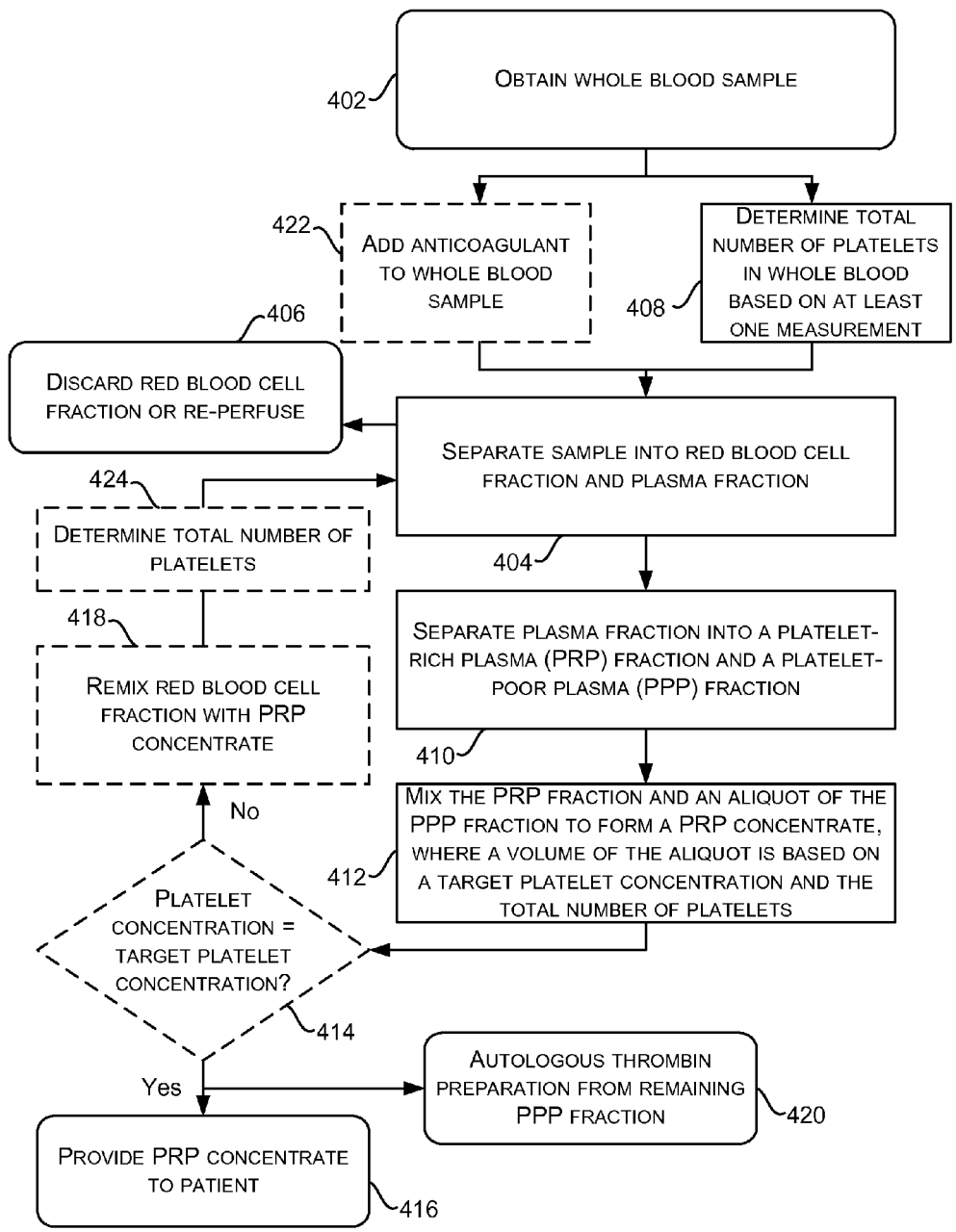
FIG. 4 illustrates yet another method for generating a PRP concentrate of a specific platelet concentration.

FIG. 4 illustrates yet another method for generating a PRP concentrate of a specific platelet concentration. The method 400 is nearly identical to the methods 200 and 300 with the primary exception that the determine operation 408 takes place on the whole blood sample, before either of the separation operations 404, 410.

Another distinction from the methods 200 and 300 is that the determine total number of platelets in whole blood sample based on at least one measurement operation 408 can be carried out in parallel with an optional add anticoagulant to whole blood sample operation 422. Alternatively, both operations 408, 422 can be carried out at overlapping or non-overlapping times between an obtain whole blood sample operation 402 and the first separation operation 404.

A final distinction is that after an optional remix red blood cell fraction with PRP concentrate operation 418, the method 400 may include an optional determine total number of platelets operation 424. This operation 424 can determine a total number of platelets in the mixture of RBCs and the PRP concentrate after they have been remixed, in the event that the PRP concentrate does not fall within a target concentration range according to a decision 414. In some embodiments, the first and second separation operations 404, 410 can be performed in a single operation by a single separation component (e.g., a centrifuge that creates an RBC fraction, a PRP fraction, and a PPP fraction).

Figure 5:
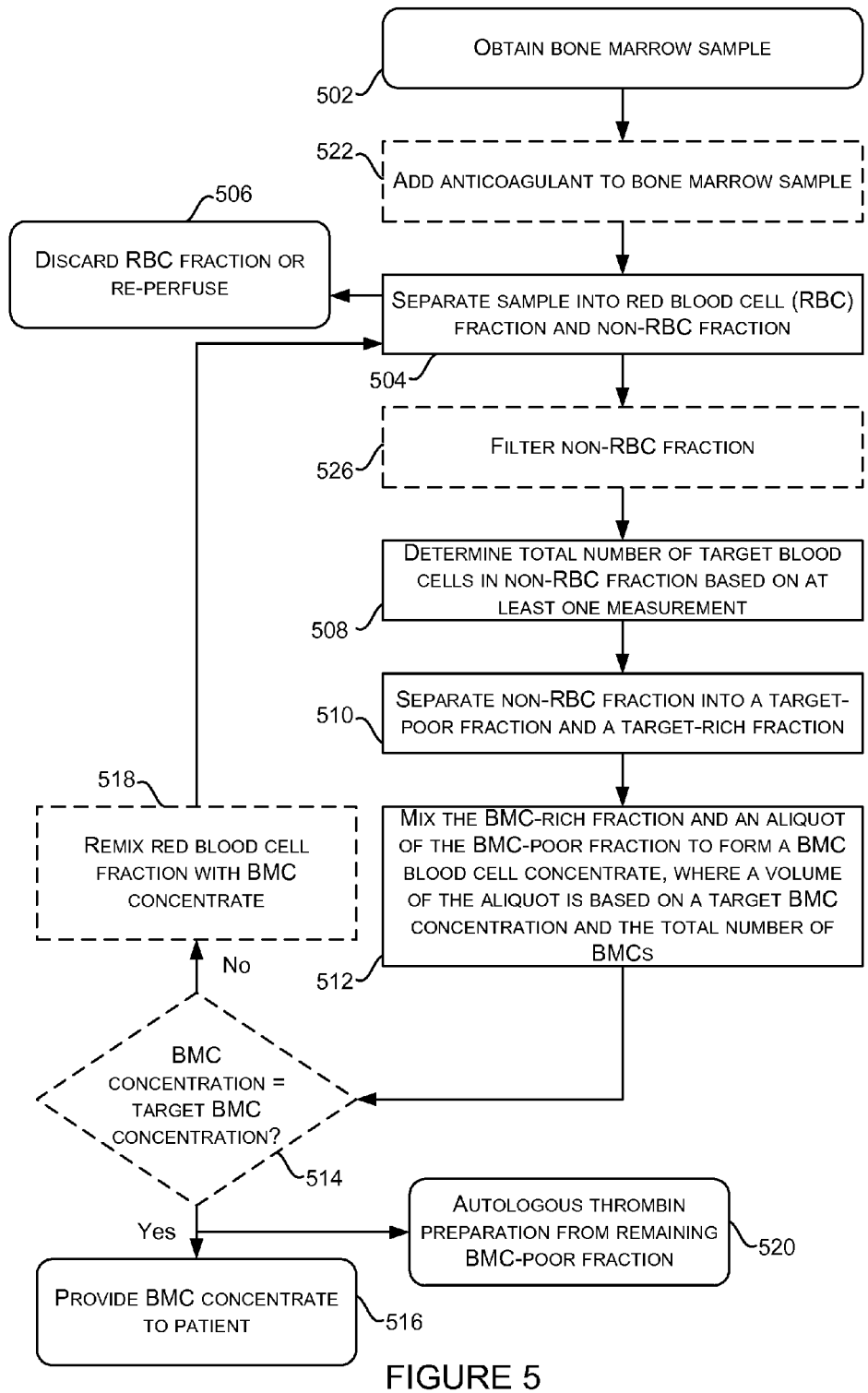
FIG. 5 illustrates a method for generating a BMC-rich concentrate of a specific BMC concentration.

FIG. 5 illustrates a method for generating a BMC-rich concentrate of a specific BMC concentration. The method 500 includes obtaining a BMC sample in obtain sample operation 502 and optionally adding an anticoagulant in add anticoagulant operation 522. Then a first separation operation 504 separates the sample into a red blood cell (RBC) fraction and a plasma fraction. The RBC fraction can be discarded or re-perfused into a patient in a discard or re-perfuse operation 506.

The total number of BMCs, $BMC_{total}$, in the plasma fraction is determined in determine operation 508. This operation 508 utilizes at least one measurement such as a concentration measured by a hemoanalysis apparatus. The BMC concentration, $BMC_0$, can be multiplied by a volume, $V_0$, of the liquid, as measured by a flow meter for instance, from which the concentration measurement was made. The volume, $V_0$, times the concentration, $BMC_0$, gives a total number of BMCs, $BMC_{total}$. The plasma fraction is then separated further via second separation operation 510 (e.g., microfluidic channel separation or centrifugation), in which a BMC-rich plasma fraction (high concentration of BMCs) and a BMC-poor plasma fraction (negligible BMC concentration) are generated.

The BMC-rich fraction and an aliquot, $V_{BMC-}$, of the BMC-poor fraction are mixed in mix operation 512. The volume of the aliquot, $V_{BMC-}$, can be based on a target BMC concentration, $BMCC_f$, and a total number of BMCs, $BMC_{total}$ (e.g., Equation (7)). The mix operation 512 forms a BMC concentrate which can then be provided to a patient in provide BMC concentrate to patient operation 516. The remaining BMC-poor fraction can also be used to form an autologous thrombin preparation for implantation into a patient in an autologous thrombin preparation operation 520.

Optionally, after the BMC concentrate is formed in mix operation 512, the BMC concentration can be checked to ensure that the BMC concentration falls within a target range (or within a margin of error of a target BMC concentration) in an optional decision 514. If the decision 514 finds that the BMC concentrate falls within the target range or within a margin of error of the target concentration, then the BMC concentrate can be provided to a patient. If not, then the concentrate can be remixed with the BMC fraction and the process can be repeated starting with the first separation operation 504.

Since settling may cause the concentrate to separate at least partially into a BMC-poor layer and a BMC-rich layer, an agitation operation may optionally be used to suspend the BMCs prior to infusion. The method may also include an optional filter plasma fraction operation 524 after the first separation operation 504. The optional filter operation 526 may remove any remaining fat and/or large particles. A 170-260 μm filter can be used in one instance.

Figure 6:
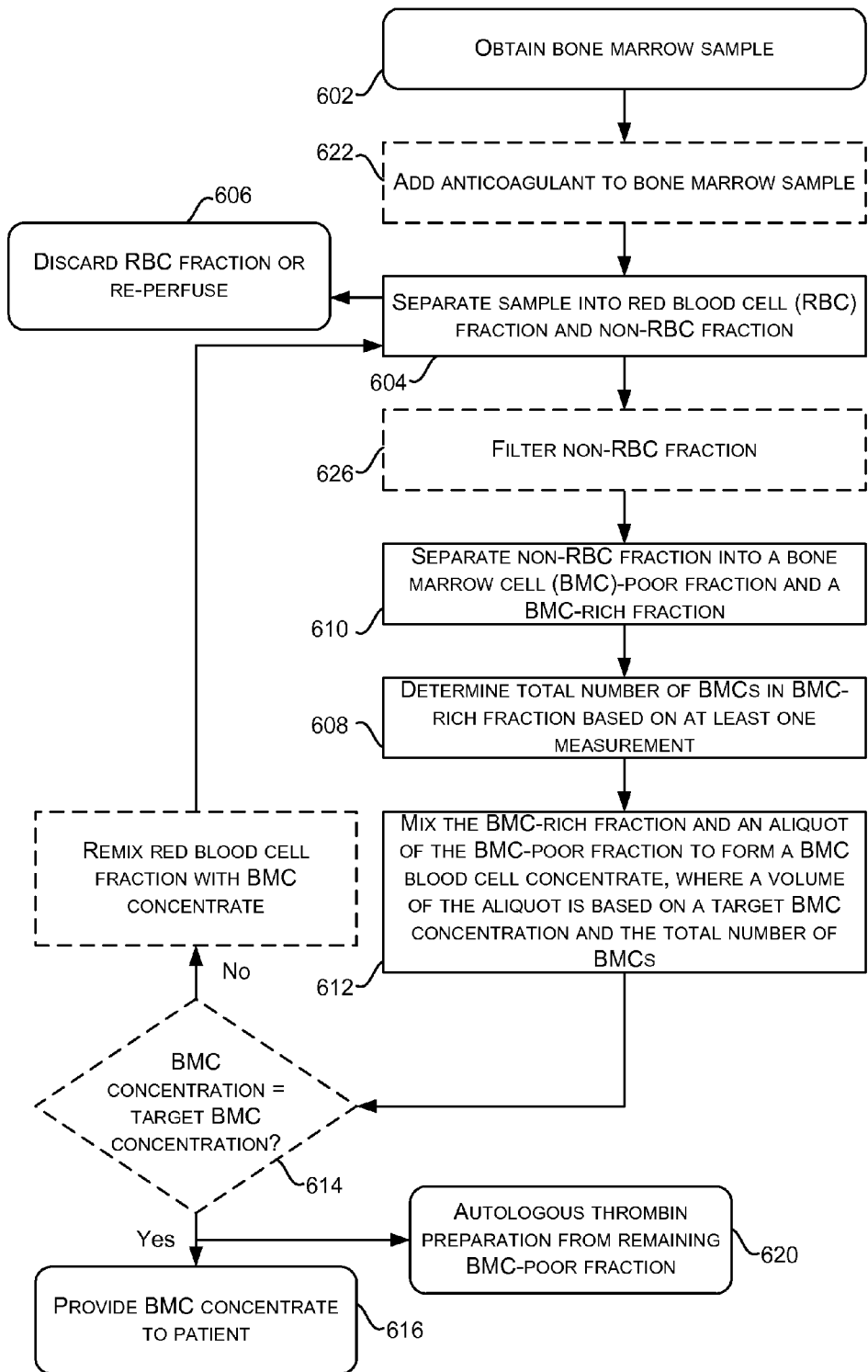
FIG. 6 illustrates another method for generating a BMC concentrate of a specific BMC concentration.

FIG. 6 illustrates another method for generating a BMC concentrate of a specific BMC concentration. The method 600 is nearly identical to the method 500 with the exception that the determine operation 608 takes place on the BMC fraction after the second separation operation 610, rather than between the first and second separation operations 604, 610.

Figure 7:
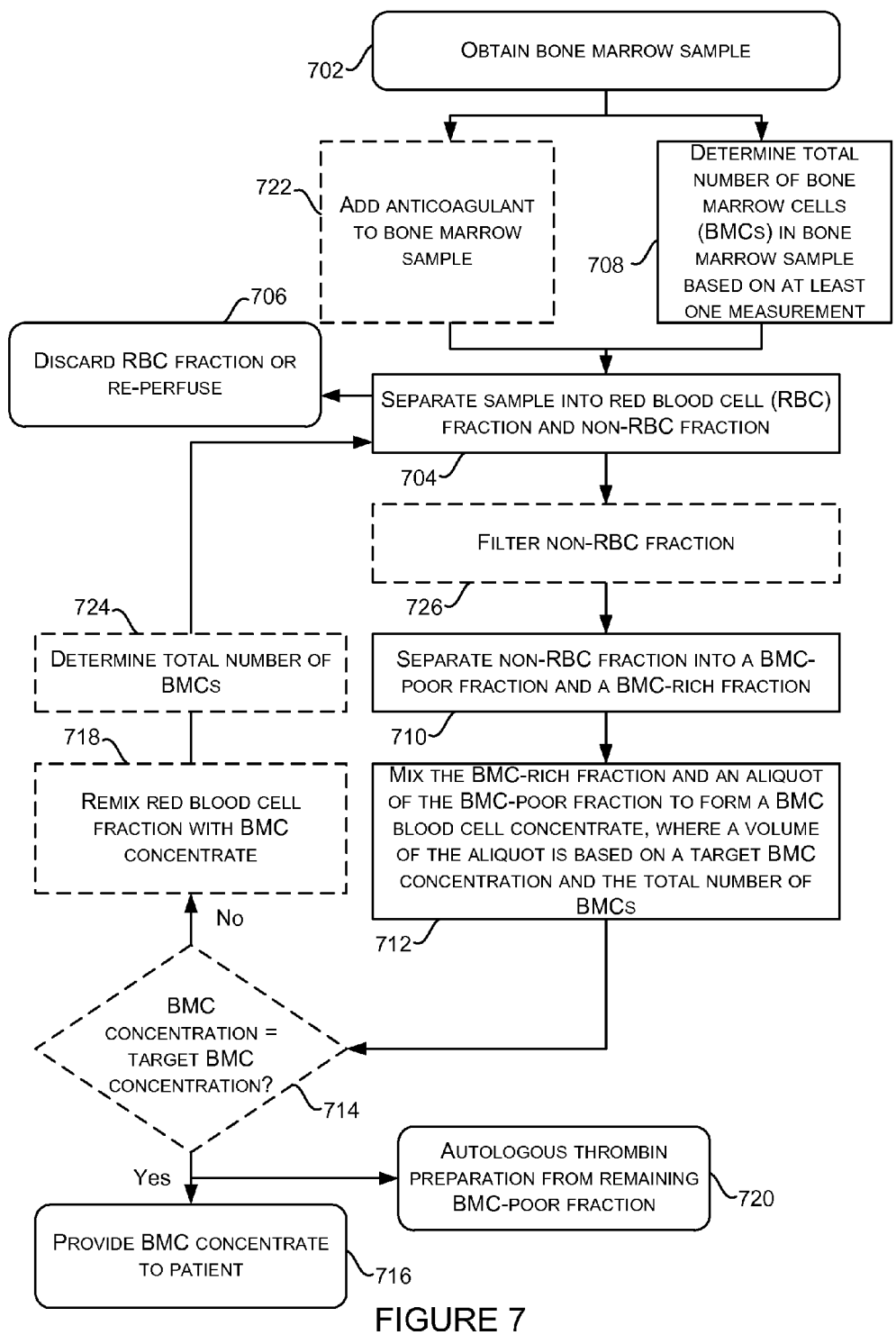
FIG. 7 illustrates yet another method for generating a BMC concentrate of a specific BMC concentration.

FIG. 7 illustrates yet another method for generating a BMC concentrate of a specific BMC concentration. The method 700 is nearly identical to the methods 500 and 600 with the primary exception that the determine operation 708 takes place on the whole bone marrow sample, before either of the separation operations 704, 710.

Another distinction from the methods 500 and 600 is that the determine total number of BMC in bone marrow sample based on at least one measurement operation 708 can be carried out in parallel with an optional add anticoagulant to bone marrow sample operation 722. Alternatively, both operations 708, 722 can be carried out at any overlapping or non-overlapping times between the obtain bone marrow sample operation 702 and the first separation operation 704.

A final distinction is that after an optional remix red blood cell fraction with BMC concentrate operation 718, the method 700 may include an optional determine total number of BMCs operation 724. This operation 724 can determine a total number of BMCs in the mixture of RBCs and the BMC concentrate after they have been remixed, in the event that the BMC concentrate does not fall within a target concentration range according to decision 714.

Figure 8:
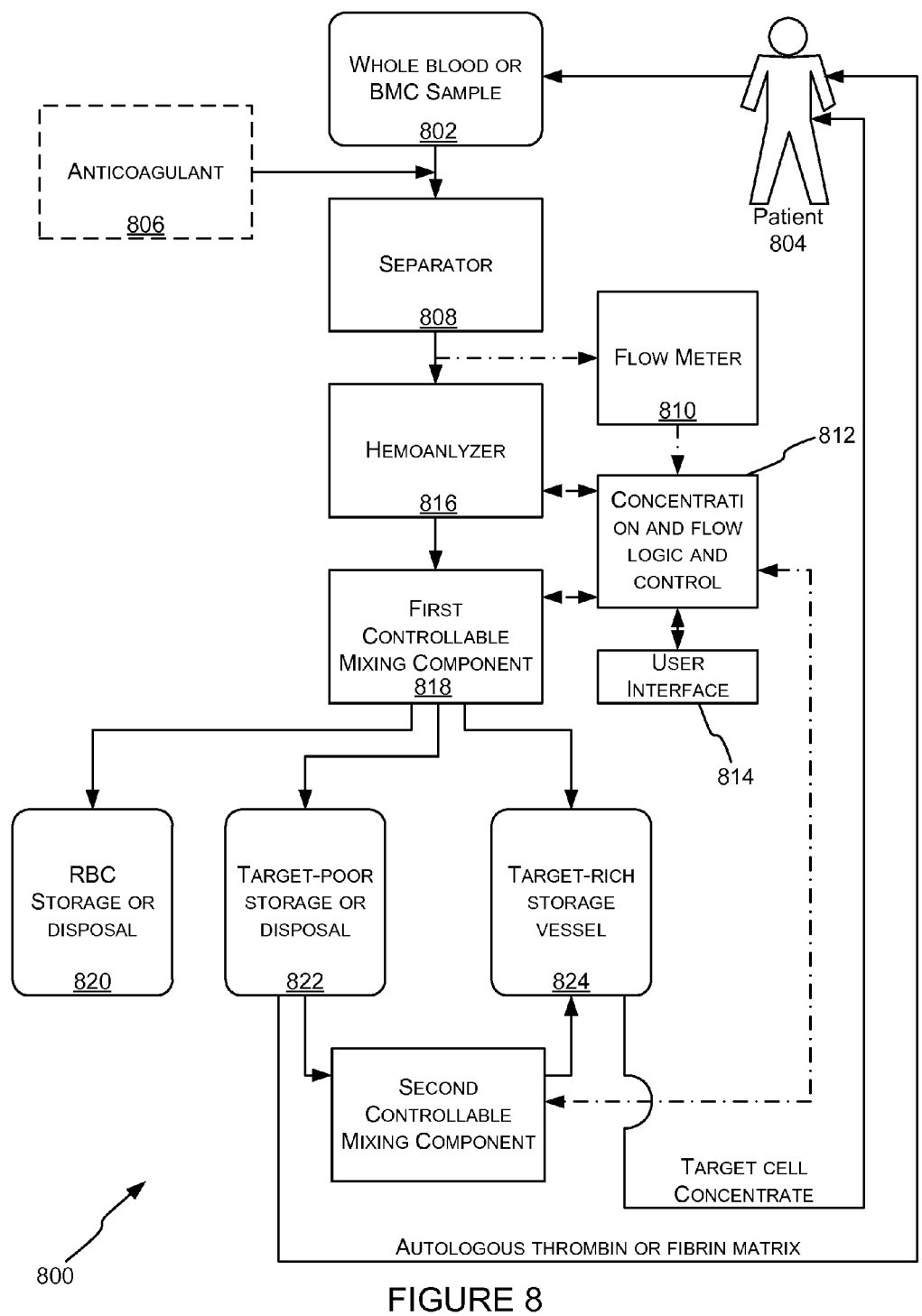
FIG. 8 illustrates a block diagram representation of another system for generating a target concentration and/or volume of platelets or bone marrow cells (BMCs).

FIG. 8 illustrates a block diagram representation of another system 800 for generating a target concentration and/or volume of platelets or bone marrow cells (BMCs). The system 800 obtains or is provided with a whole blood sample or a BMC sample 802 from a patient 804. The sample can optionally be mixed with an anticoagulant 806 before entering a separator 808 (e.g., microfluidic channels or centrifuge, to name two).

The separator 808 can separate the sample 802 into two fractions: a red blood cell (RBC) fraction and a plasma fraction. The separator 808 can also separate the sample 802 into three fractions: an RBC fraction, a target cell-poor fraction, and a target cell-rich fraction. Target cells are the ones that are desired to be in a particular concentration in the final concentrate. For instance, platelets, white blood cells, bone marrow cells, pluripotent cells, and stem cell-like cells are a few exemplary target cells. Any cell found in a bone marrow sample can be a target cell. The target cell-poor fraction is one having a negligible concentration of target cells while the target cell-rich fraction has a greater-than-natural concentration of target cells.

As each fraction leaves the separator 808, a flow meter 810 can measure a volume of fluid leaving the separator 808. This data can be passed on to a concentration and flow logic and control component 812. The concentration and flow logic and control 812 controls a first controllable mixing component 818 in order to control a flow of fluid. The flow logic and control 812 also determines a total number of target cells by multiplying a concentration of target cells leaving the separator 808 by a volume of the fluid leaving the separation 808. The flow logic and control 812 further determines how fluids are to be mixed and in what amounts in order to obtain a target concentration of the target cells.

Data representing flow rates, concentrations, volumes, and other parameters can be displayed to a user via the user interface 814.

The concentration of various particles and cells within each fraction is measured by a hemoanalyzer 818. The hemoanalyzer 818 can be embodied in a variety of devices and methods, such as fluorescent activated cell sorting (FACS), optical microscopy, optical light scattering, and electrical impedance, to name a few. The concentrations measured by the hemoanalyzer 816 are passed to the concentration and flow logic and control 812, which uses these measurements to determine a total number of target cells in the fluid. From this total number of target cells, the concentration and flow logic and control 812 can determine instructions for a first controllable mixing component 818 (e.g., pump or valve or combination of the two).

The first controllable mixing component 818 directs the RBC fraction into an RBC storage or disposal vessel 820. It also directs the target-poor fraction into a target-poor storage or disposal vessel 822. Finally it directs the target-rich fraction into a target-rich storage vessel 824. The order in which these three fractions are directed into their respective vessels 820, 822, 824 is not limiting and thus any combination or order is envisioned.

The concentration and flow logic control 812 also instructs a second controllable mixing component (e.g., pump, valve, or combination of the two) to add an aliquot of the target-poor fraction to the entire target-rich fraction within the target-rich storage vessel 824. The volume of the aliquot is selected so that the combination within the target-rich storage vessel 824 has a concentration or concentration range of the target cell that meets a target concentration or target concentration range.

When this target concentration or concentration range is achieved, a target cell concentrate exists in the target-rich storage vessel 824 and can be provided to the patient 804 (or another patient). The remaining target-poor fraction in the target-poor storage or disposal vessel 822 can also be provide to the patient 804 (or another patient) as an autologous thrombin or a fibrin matrix.

Figure 9:
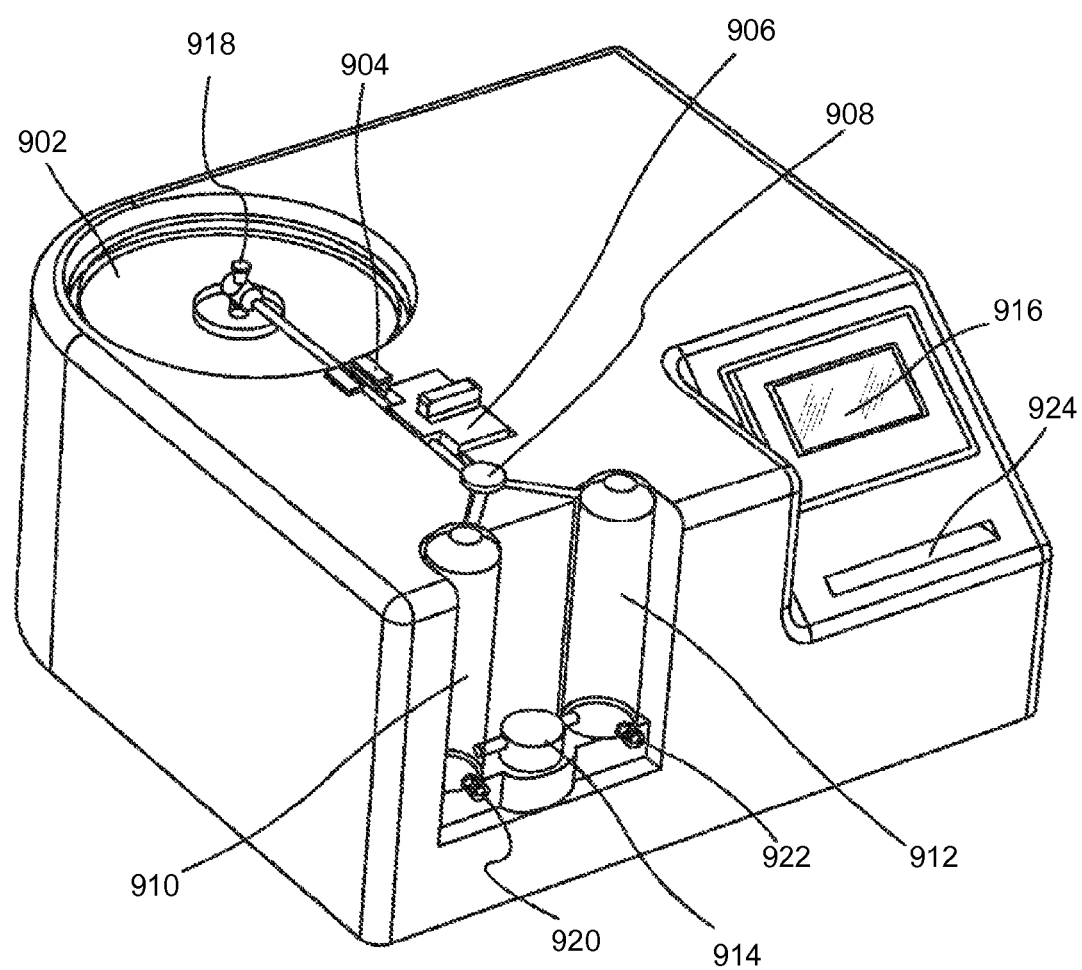
FIG. 9 illustrates a PRP or BMC concentrating apparatus.
Figure 9:

FIG. 9 illustrates a PRP or BMC concentrating apparatus 900. The apparatus 900 includes a disc centrifuge 902 for separating a whole blood or BMC sample. The disc centrifuge 902 can separate the sample into a red blood cell (RBC) fraction (outside layer), a platelet-rich plasma (PRP) or BMC-rich fraction (middle layer), and a platelet-poor plasma (PPP) fraction or BMC-poor fraction (inner layer). The whole blood or bone marrow sample can be provided to the centrifuge via an opening 918, which can accept the needle of a syringe, for instance. The opening 918 can be configured such that it is in a closed state unless the needle of a syringe is placed into the opening, thus allowing fluid to be passed into the disc centrifuge 902, but not to escape via the opening.

The PPP or BMC-poor fraction can be removed first, and can pass through a flow meter 904 and a hemotology analyzer module 906 to a first vessel 910. Fluid can pass through the flow meter 904 or the hemotology analyzer module 906 in any order, although as illustrated, flow is first through the flow meter 904. The flow meter 906 provides volume of the PPP or BMC-poor fraction. The removal and flow of the PPP or BMC-poor fraction can be controlled by a computer controlled valve/pump 908.

Once the PPP or BMC-poor fraction has been removed from the disc centrifuge 902, the PRP or BMC-rich fraction becomes the lower or innermost layer, and can be removed next. The PRP or BMC-rich fraction passes through the flow meter 906 providing a volume of the PRP or BMC-rich fraction to logic of the apparatus 900 (e.g., a processor). The PRP or BMC-rich fraction can also pass through a hemotology analyzer module 906 that measures a total number of platelets or BMCs in the PRP or BMC-rich fraction. Given this volume and total number of platelets or BMCs, logic within the apparatus can determine a concentration of platelets or BMCs within the PRP or BMC-rich fraction as the total number of platelets or BMCs times the volume of the PRP or BMC-rich fraction. The PRP or BMC-rich fraction can be directed to a second vessel 912. The removal and flow of the PRP or BMC-rich fraction can be controlled by the computer controlled valve/pump 908.

The RBC fraction can remain in the disc centrifuge, and since the centrifuge is disposable, no further action need be taken relative to the RBC fraction. The logic within the apparatus 900 can determine an aliquot of the PPP fraction, or of the BMC-poor fraction, to be mixed with the PRP or BMC-rich fraction in order to achieve a target platelet or BMC concentration. In one embodiment, a user can set the target concentration via a user interface 916 (see FIG. 12). A second computer controlled valve/pump 914 can allow the aliquot to pass from the first vessel 910 to the second vessel 912 in order to form the PRP or BMC concentrate. An optional agitation mechanism (not illustrated) may be activated to improve mixing of the PRP or BMC concentrate within the second vessel 912.

Figure 13:
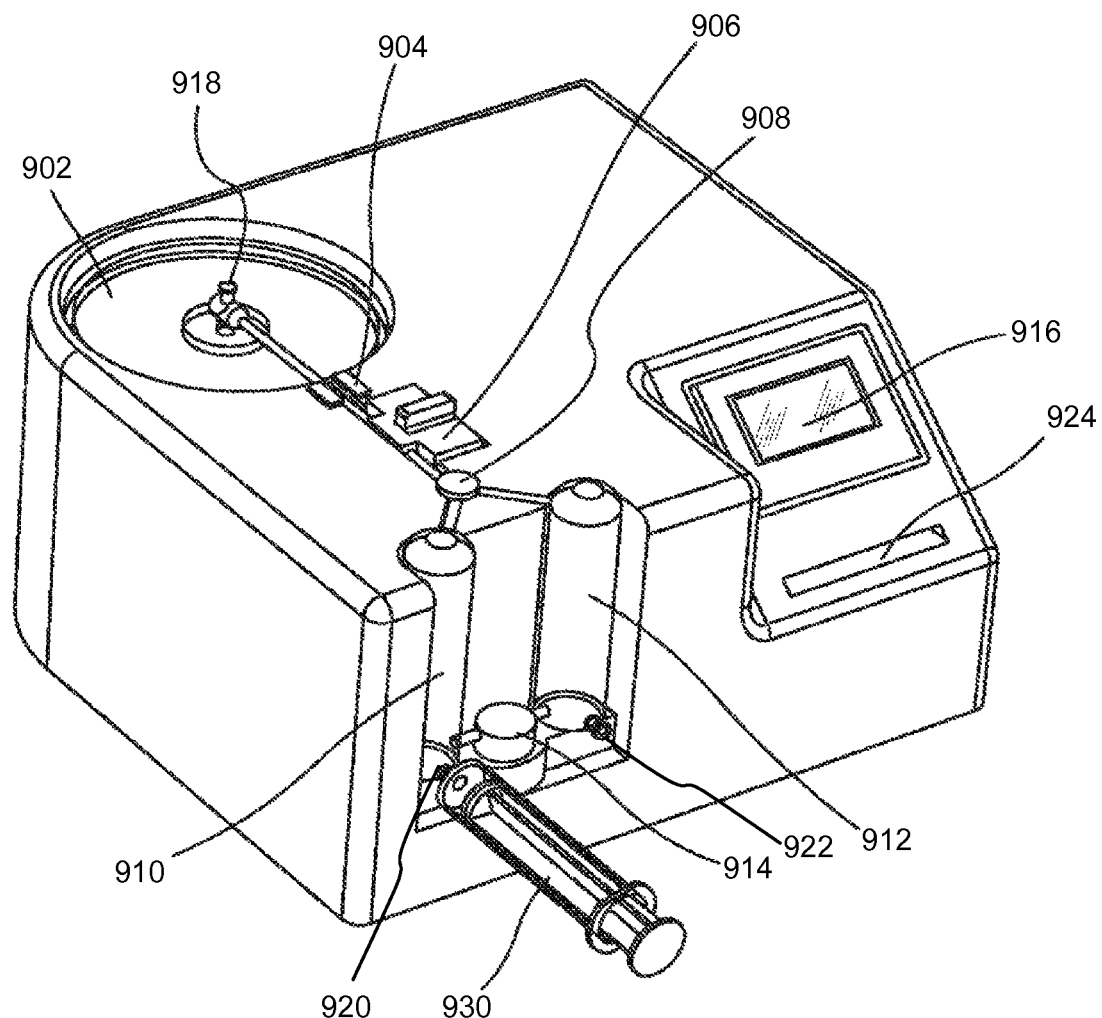
FIG. 13 illustrates how a syringe can be used to remove contents of the first vessel illustrated in FIGS. 9-13.

The remaining PPP fraction or BMC-poor fraction and the PRP or BMC concentrate can be removed from the vessels 910, 912 via respective openings 920 and 922, which may be accessible via the needle of a syringe in one embodiment (see FIG. 13). At the same time, the vessels 910, 912 may be separable and removable such that they can each be moved to a patient or storage location for later use.

Although FIG. 9 has been described where fluid is removed from the disc centrifuge 902 from a middle of the centrifuge 902, in other embodiments, fluid can leave the disc centrifuge from other points. For instance, fluid can leave from an outer radius of the centrifuge in some embodiments. Also, the order of removing different fractions can be varied. In some embodiments, a printer 924 can provide hardcopies of data from the apparatus 900.

Figure 10:
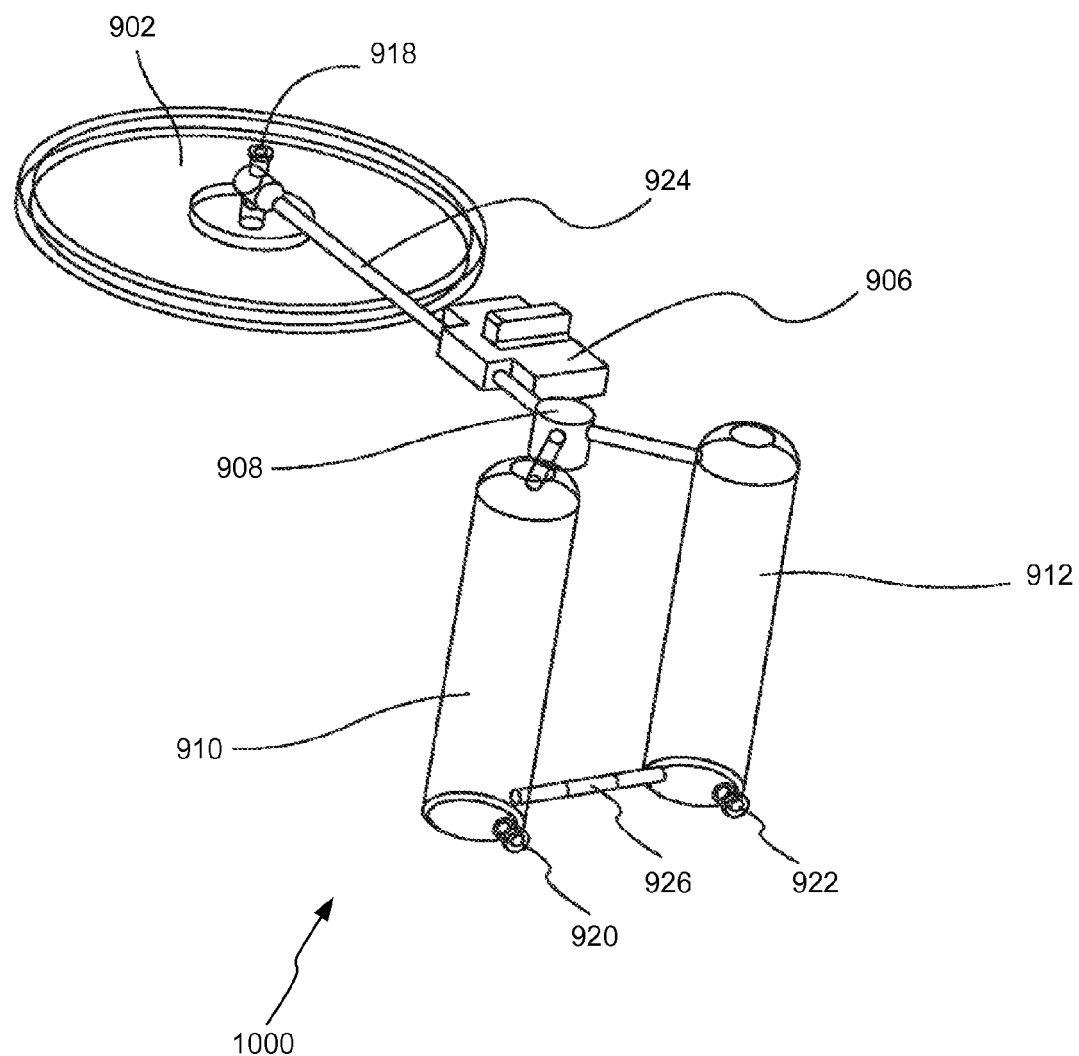
FIG. 10 illustrates one embodiment of a package comprising those components of the apparatus that can be disposable.

To ensure sterility, those portions of the apparatus 900 that contact blood or bone marrow can be modular and disposable. FIG. 10 illustrates one embodiment of a package 1000 comprising those components of the apparatus 900 that can be disposable. These can include any one or more of the following illustrated components: the centrifuge 902, the centrifuge opening 918, the hematology analyzer module 906, the first computer controlled valve/pump 908, and the first and second vessels 910, 912. Additionally, the disposable portions of the apparatus 900 can include a fluid path 924 between the centrifuge 902 and the computer-controlled valve/pump 908, and a fluid path 926 connecting the first and second vessels 910, 912. Any two or more of these components can be interlinked to simplify and ease installation, removal, and transport, and the interlinked package 1000 can be replaced by a similar or identical package 1000.

Figure 11:
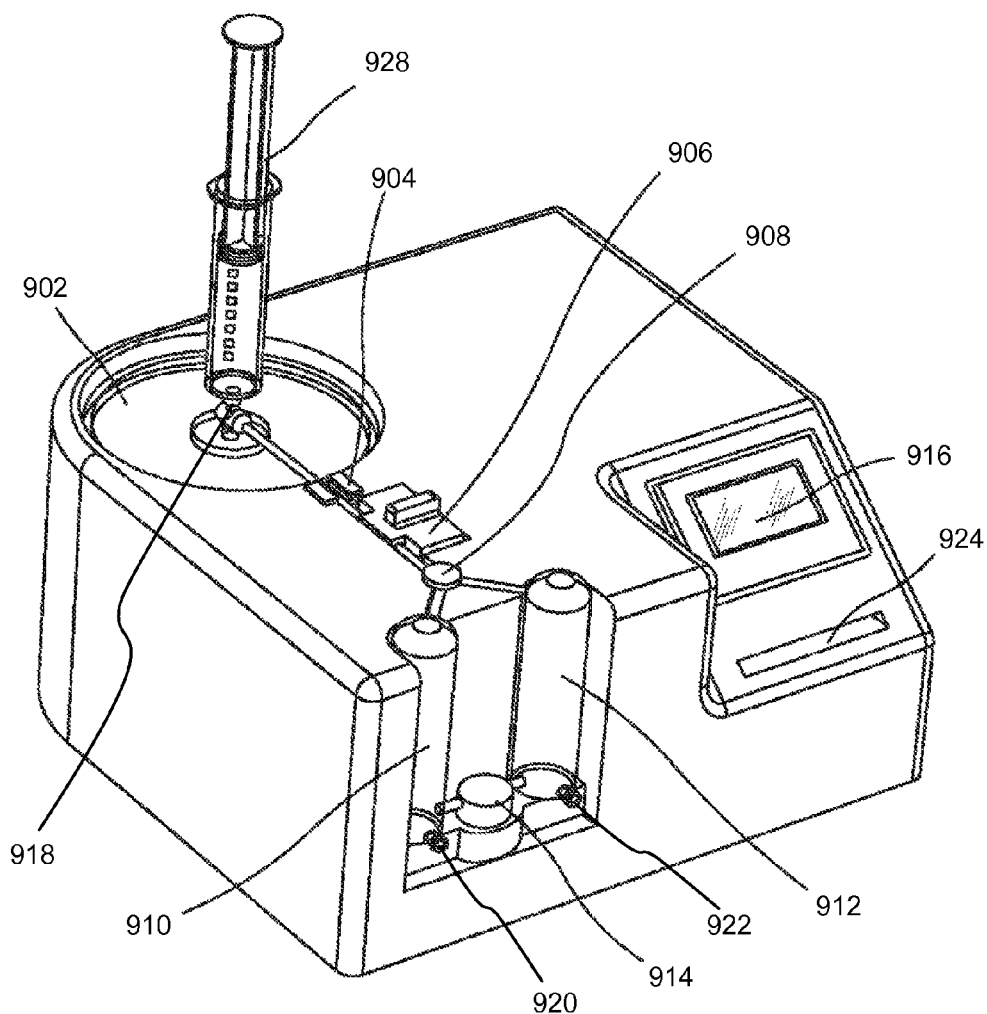
FIG. 11 illustrates how a syringe can be used to provide a whole blood or bone marrow sample to the apparatus of FIG. 9.

FIG. 11 illustrates how a syringe 928 can be used to provide a whole blood or bone marrow sample to the apparatus 900 of FIG. 9 via insertion through the opening 918.

Figure 12:
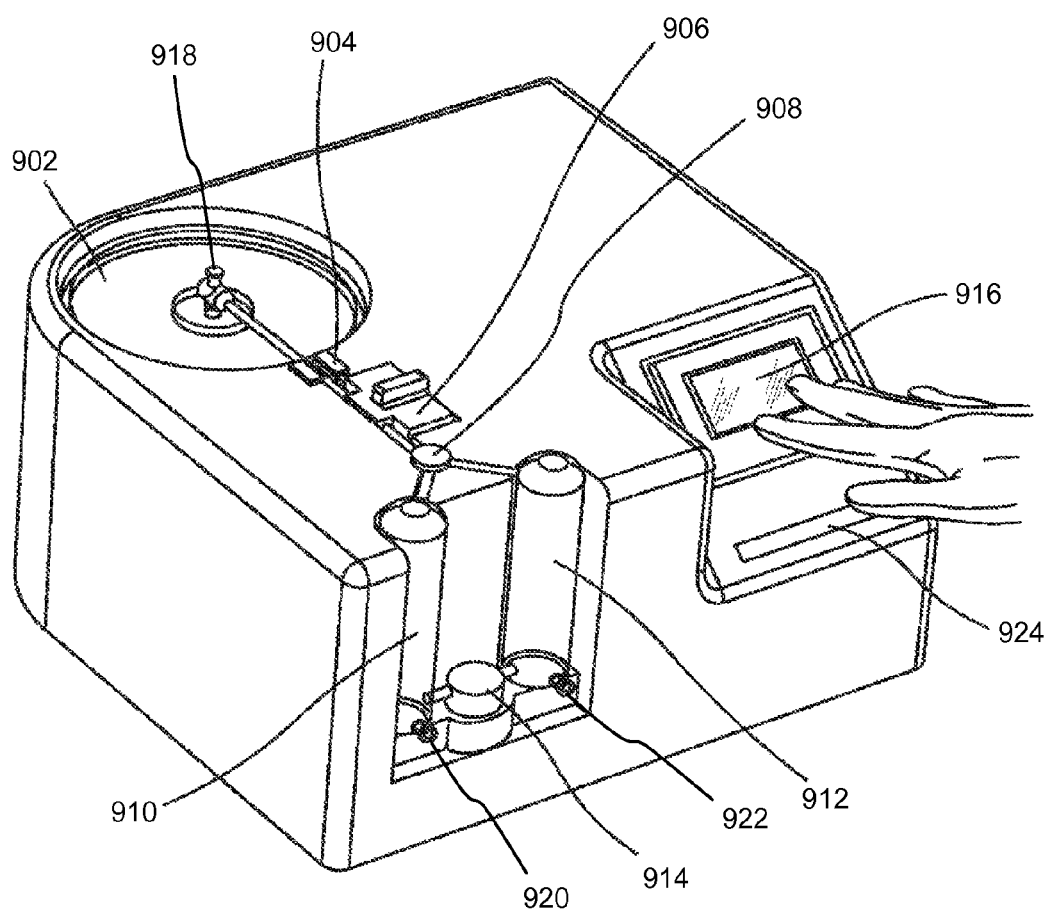
FIG. 12 illustrates a user interacting with the apparatus of FIG. 9, for instance, via a touchscreen embodiment of the user interface.
Figure 12:

FIG. 12 illustrates a user interacting with the apparatus 900 of FIG. 9, for instance, via a touchscreen embodiment of the user interface 916.

FIG. 13 illustrates how a syringe 930 can be used to remove contents of the first vessel 910 illustrated in FIGS. 9-13. As described, the first vessel 910 can hold a PPP fraction or a BMC-poor fraction, and the syringe can be used to extract a part or all of the contents of the first vessel 910.

While FIGS. 9-13 have described the first vessel 910 as typically storing the PPP or BMC-poor fraction, and the second vessel 912 as storing the PRP or BMC-rich fraction or PRP or BMC concentrate, one of skill in the art will recognize that the two vessels 910, 912 are interchangeable and thus not limited to a right or left of the apparatus 900.

Figure 14:
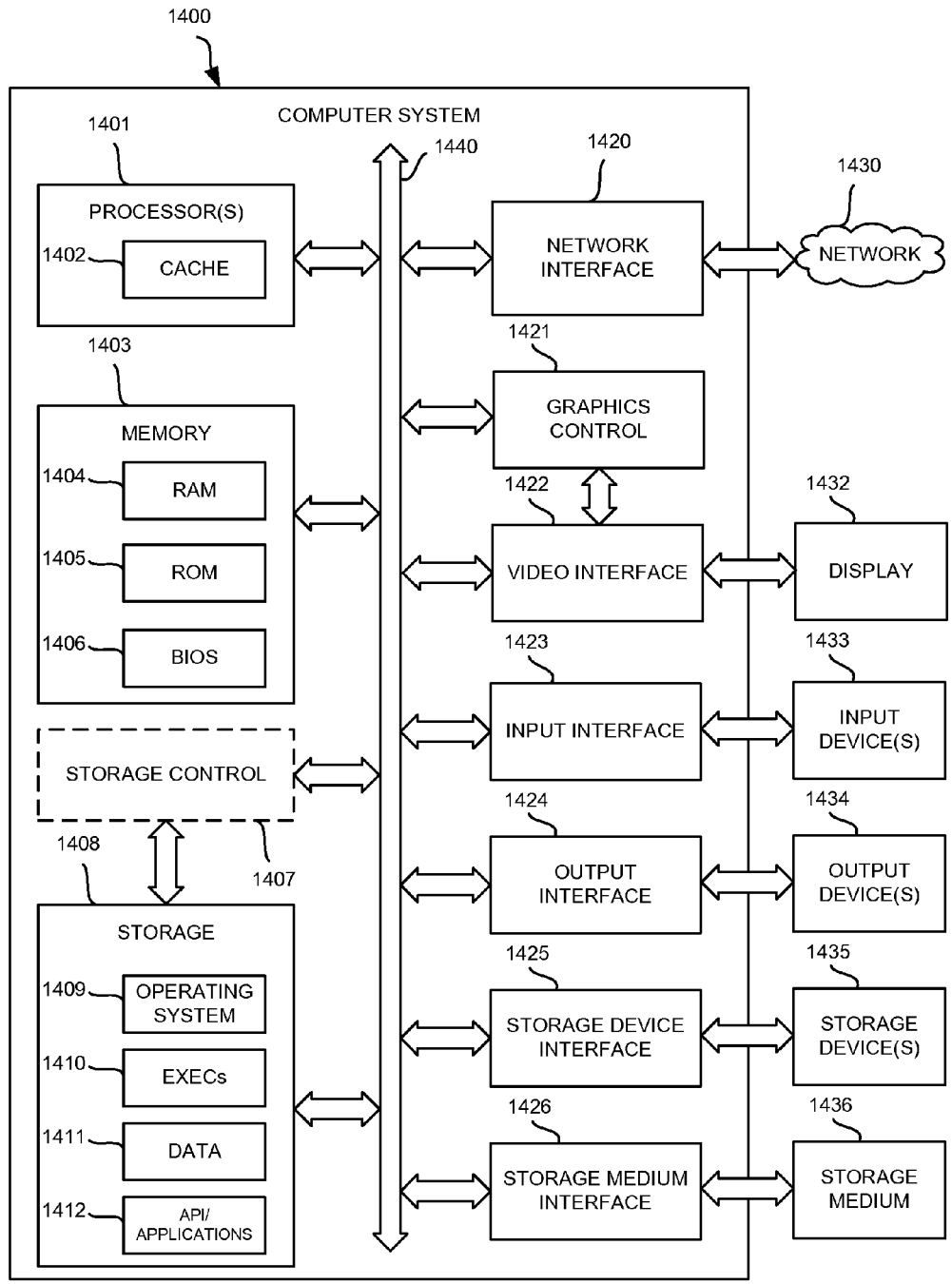
FIG. 14 shows a diagrammatic representation of one embodiment of a machine in the exemplary form of a computer system within which a set of instructions can execute for causing a device to perform or execute any one or more of the aspects and/or methodologies of the present disclosure.

The systems and methods described herein can be implemented in a machine such as a computer system in addition to the specific physical devices described herein. FIG. 14 shows a diagrammatic representation of one embodiment of a machine in the exemplary form of a computer system 1400 within which a set of instructions can execute for causing a device to perform or execute any one or more of the aspects and/or methodologies of the present disclosure. The components in FIG. 14 are examples only and do not limit the scope of use or functionality of any hardware, software, embedded logic component, or a combination of two or more such components implementing particular embodiments.

Computer system 1400 may include a processor 1401, a memory 1403, and a storage 1408 that communicate with each other, and with other components, via a bus 1440. The bus 1440 may also link a display 1432, one or more input devices 1433 (which may, for example, include a keypad, a keyboard, a mouse, a stylus, etc.), one or more output devices 1434, one or more storage devices 1435, and various tangible storage media 1436. All of these elements may interface directly or via one or more interfaces or adaptors to the bus 1440. For instance, the various tangible storage media 1436 can interface with the bus 1440 via storage medium interface 1426. Computer system 1400 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 1401 (or central processing unit(s) (CPU(s))) optionally contains a cache memory unit 1402 for temporary local storage of instructions, data, or computer addresses. Processor(s) 1401 are configured to assist in execution of computer readable instructions. Computer system 1400 may provide functionality as a result of the processor(s) 1401 executing software embodied in one or more tangible computer-readable storage media, such as memory 1403, storage 1408, storage devices 1435, and/or storage medium 1436. The computer-readable media may store software that implements particular embodiments, and processor(s) 1401 may execute the software. Memory 1403 may read the software from one or more other computer-readable media (such as mass storage device(s) 1435, 1436) or from one or more other sources through a suitable interface, such as network interface 1420. The software may cause processor(s) 1401 to carry out one or more processes or one or more steps of one or more processes described or illustrated herein. Carrying out such processes or steps may include defining data structures stored in memory 1403 and modifying the data structures as directed by the software.

The memory 1403 may include various components (e.g., machine readable media) including, but not limited to, a random access memory component (e.g., RAM 1404) (e.g., a static RAM "SRAM", a dynamic RAM "DRAM", etc.), a read-only component (e.g., ROM 1405), and any combinations thereof. ROM 1405 may act to communicate data and instructions unidirectionally to processor(s) 1401, and RAM 1404 may act to communicate data and instructions bidirectionally with processor(s) 1401. ROM 1405 and RAM 1404 may include any suitable tangible computer-readable media described below. In one example, a basic input/output system 1406 (BIOS), including basic routines that help to transfer information between elements within computer system 1400, such as during start-up, may be stored in the memory 1403.

Fixed storage 1408 is connected bidirectionally to processor(s) 1401, optionally through storage control unit 1407. Fixed storage 1408 provides additional data storage capacity and may also include any suitable tangible computer-readable media described herein. Storage 1408 may be used to store operating system 1409, EXECs 1410 (executables), data 1411, API applications 1412 (application programs), and the like. Often, although not always, storage 1408 is a secondary storage medium (such as a hard disk) that is slower than primary storage (e.g., memory 1403). Storage 1408 can also include an optical disk drive, a solid-state memory device (e.g., flash-based systems), or a combination of any of the above. Information in storage 1408 may, in appropriate cases, be incorporated as virtual memory in memory 1403.

In one example, storage device(s) 1435 may be removably interfaced with computer system 1400 (e.g., via an external port connector (not shown)) via a storage device interface 1425. Particularly, storage device(s) 1435 and an associated machine-readable medium may provide nonvolatile and/or volatile storage of machine-readable instructions, data structures, program modules, and/or other data for the computer system 1400. In one example, software may reside, completely or partially, within a machine-readable medium on storage device(s) 1435. In another example, software may reside, completely or partially, within processor(s) 1401.

Bus 1440 connects a wide variety of subsystems. Herein, reference to a bus may encompass one or more digital signal lines serving a common function, where appropriate. Bus 1440 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1400 may also include an input device 1433. In one example, a user of computer system 1400 may enter commands and/or other information into computer system 1400 via input device(s) 1433. Examples of an input device(s) 1433 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 1433 may be interfaced to bus 1440 via any of a variety of input interfaces 1423 (e.g., input interface 1423) including, but not limited to, serial, parallel, game port, USB, FIREWIRE, a THUNDERBOLT hardware interface (THUNDERBOLT is a registered trademark of Intel Corporation), or any combination of the above.

In particular embodiments, when computer system 1400 is connected to network 1430, computer system 1400 may communicate with other devices, specifically mobile devices and enterprise systems, connected to network 1430. Communications to and from computer system 1400 may be sent through network interface 1420. For example, network interface 1420 may receive incoming communications (such as requests or responses from other devices) in the form of one or more packets (such as Internet Protocol (IP) packets) from network 1430, and computer system 1400 may store the incoming communications in memory 1403 for processing. Computer system 1400 may similarly store outgoing communications (such as requests or responses to other devices) in the form of one or more packets in memory 1403 and communicated to network 1430 from network interface 1420. Processor(s) 1401 may access these communication packets stored in memory 1403 for processing.

Examples of the network interface 1420 include, but are not limited to, a network interface card, a modem, and any combination thereof. Examples of a network 1430 or network segment 1430 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 1430, may employ a wired and/or a wireless mode of communication. In general, any network topology may be used.

Information and data can be displayed through a display 1432. Examples of a display 1432 include, but are not limited to, a liquid crystal display (LCD), an organic liquid crystal display (OLED), a cathode ray tube (CRT), a plasma display, and any combinations thereof. The display 1432 can interface to the processor(s) 1401, memory 1403, and fixed storage 1408, as well as other devices, such as input device(s) 1433, via the bus 1440. The display 1432 is linked to the bus 1440 via a video interface 1422, and transport of data between the display 1432 and the bus 1440 can be controlled via the graphics control 1421.

In addition to a display 1432, computer system 1400 may include one or more other peripheral output devices 1434 including, but not limited to, an audio speaker, a printer, and any combinations thereof. Such peripheral output devices may be connected to the bus 1440 via an output interface 1424. Examples of an output interface 1424 include, but are not limited to, a serial port, a parallel connection, a USB port, a FIREWIRE port, a THUNDERBOLT port, and any combinations thereof.

In addition or as an alternative, computer system 1400 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In conclusion, the present invention provides, among other things, systems and methods that autonomously or semi-autonomously produce a PRP or BMC concentrate having a target concentration of platelets or BMCs. Those skilled in the art can readily recognize that numerous variations and substitutions may be made in the invention, its use, and its configuration to achieve substantially the same results as achieved by the embodiments described herein. For instance, blood products can be moved through the system 100 and 800, or to other systems, either manually or autonomously. As another example, methods for separating blood components besides centrifugation can be used (e.g., microfluidic channel separation or electrical impedance separation). Accordingly, there is no intention to limit the invention to the disclosed exemplary forms. Many variations, modifications, and alternative constructions fall within the scope and spirit of the disclosed invention.

What is claimed is:

1. A cell concentrating system comprising:
    a blood separation component having a blood sample input and having a centrifuge to separate the blood sample into a red blood cell fraction and a plasma fraction, the plasma fraction comprising a target cell-rich fraction and a target cell-poor fraction, the blood sample having a volume of between 60 mL and no more than 250 mL;
    a first vessel for storing the target cell-poor fraction separated from the blood sample;
    a second vessel for storing the target cell-rich fraction separated from the blood sample;
    a first valve upstream of the first vessel and the second vessel, and downstream of the blood separation component;
    a second valve for providing selective fluid communication between the first vessel and the second vessel;
    a concentration and flow logic and control component comprising a concentration measurement component, a partial separation component, and a controller, the concentration measurement component comprising at least one of a fluorescent activated cell sorting component and an optical sensor, the partial separation component comprising a microfluidic channel device for separating particles within the blood sample and a light scattering device for measuring a number of particles in the blood sample, and the controller comprising a processor and memory configured to:
        control the first valve to remove the target cell-poor fraction to the first vessel and to remove the target cell-rich fraction to the second vessel;
        determine, via the controller, a first volume of the target cell-poor fraction in the first vessel to mix with the target cell-rich fraction in the second vessel in order to form a target cell-rich concentrate having a concentration of target cells that is within a target concentration range for studying or defining a dose-response relationship in a patient, wherein the first volume is determined by the controller via information from a flow meter or from a calculation based upon a known concentration of the blood sample and a known volume of the blood sample that is in the memory of the controller;
        determine, via the concentration measurement component, whether the target cell-rich concentrate has a concentration of target cells within the target concentration ranges wherein the concentration is determined by the controller via information from the flow meter and a hematology analyzer;
        control, via the controller, the second valve to transfer the first volume of the target cell-poor cell rich fraction from the first vessel to the second vessel to form the target cell-rich concentrate; and
    wherein the target concentration range is between 1.0 and $1.5 \times 10^6$ target cells/uL.

2. The cell concentrating system of claim 1, wherein the blood sample is a whole blood sample or a bone marrow sample.

3. The cell concentrating system of claim 1,
    wherein the concentration measurement component comprises the flow meter component that measures a second volume in which the concentration was measured.

4. The cell concentrating system of claim 3, wherein the concentration measurement component measures a concentration of target cells in the target cell-rich fraction and the second volume is that of the target cell-rich fraction.

5. The cell concentrating system of claim 3, wherein the concentration measurement component is configured to perform a function selected from the group consisting of optical microscopy, optical light scattering, and electrical impedance.

6. The cell concentrating system of claim 1, wherein the target cells are selected from the group consisting of: pluripotent cells, white blood cells, platelets, Neutrophils, Monocytes, Lymphoctyes, Eosinophils, and Basophils.

* * * * *